United States Patent [19]

Scrima et al.

[11] Patent Number: 5,416,216
[45] Date of Patent: May 16, 1995

[54] TETRAMETHYLPIPERIDINE COMPOUNDS FOR USE AS STABILISERS FOR ORGANIC MATERIALS

[75] Inventors: Roberto Scrima, Bologna; Graziano Zagnoni, Vergato-Bologna, both of Italy

[73] Assignee: Ciba-Geigy Corporation, Ardsley, N.Y.

[21] Appl. No.: 198,664

[22] Filed: Feb. 18, 1994

Related U.S. Application Data

[63] Continuation of Ser. No. 910,600, Jul. 8, 1992, abandoned.

[30] Foreign Application Priority Data

Jul. 12, 1991 [IT]  Italy ............................. MI91A01948

[51] Int. Cl.$^6$ .......................................... C07D 211/08
[52] U.S. Cl. .................................... 546/186; 546/190; 544/198
[58] Field of Search ................. 546/186, 190; 544/198

[56] References Cited

U.S. PATENT DOCUMENTS

| | | | |
|---|---|---|---|
| 3,684,765 | 8/1972 | Matsui et al. | 260/45.8 N |
| 3,904,581 | 9/1975 | Murayama et al. | 260/45.8 N |
| 4,108,829 | 8/1978 | Cassandrine et al. | 260/45.8 NT |
| 4,316,025 | 2/1982 | Cantatore et al. | 544/364 |
| 4,433,145 | 2/1984 | Wiezer et al. | 544/198 |
| 4,533,688 | 8/1985 | Toda et al. | 524/100 |
| 4,740,544 | 4/1988 | Nakahara et al. | 524/100 |
| 5,026,749 | 6/1991 | Cantatore et al. | 524/99 |
| 5,047,531 | 9/1991 | Cantatore et al. | 544/198 |

FOREIGN PATENT DOCUMENTS

| | | |
|---|---|---|
| 0112690 | 7/1984 | European Pat. Off. ............ 544/198 |
| 0117229 | 8/1984 | European Pat. Off. . |
| 0176106 | 11/1990 | European Pat. Off. . |
| 0410934 | 1/1991 | European Pat. Off. . |
| 0427674 | 5/1991 | European Pat. Off. . |
| 0455588 | 11/1991 | European Pat. Off. . |
| 0479724 | 4/1992 | European Pat. Off. . |

*Primary Examiner*—Howard T. Mars
*Assistant Examiner*—Michael B. Hydorn
*Attorney, Agent, or Firm*—Luther A. R. Hall

[57] ABSTRACT

Novel piperidine compounds of the formula (I)

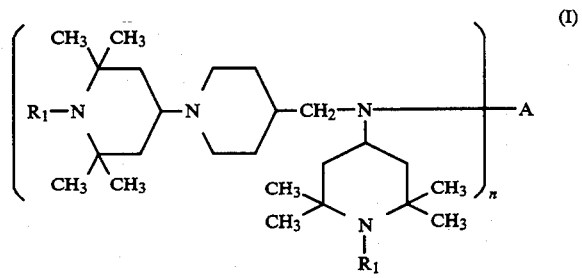

in which $R_1$ is e.g. hydrogen or methyl, n is e.g. 1 and A is e.g. —$COR_2$ with $R_2$ being $C_1$–$C_{18}$alkyl.

The said compounds are effective as light stabilisers, heat stabilizers and oxidation stabilisers for organic materials.

7 Claims, No Drawings

TETRAMETHYLPIPERIDINE COMPOUNDS FOR USE AS STABILISERS FOR ORGANIC MATERIALS

This is a continuation of application Ser. No. 07/910,600, filed on Jul. 8, 1992, now abandoned.

The present invention relates to novel piperidine compounds, to the use thereof as light stabilisers, heat stabilisers and oxidation stabilisers for organic materials, in particular synthetic polymers, and to the organic materials thus stabilised.

The stabilisation of synthetic polymers by derivatives of 2,2,6,6-tetramethylpiperidine has been described in numerous publications, in particular in U.S. Pat. Nos. 3,684,765, 3,904,581, 4,108,829, 4,316,025, 4,433,145, 4,533,688 and 4,740,544, European Laid Open Prints 117,229, 176,106 and 410,934.

The present invention relates to novel compounds of the formula (I)

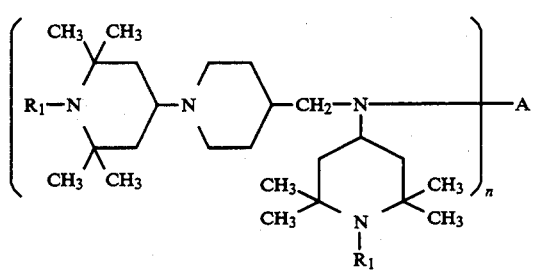

in which $R_1$ is hydrogen, $C_1$–$C_8$alkyl, O, OH, NO, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or mono-, di- or tri-substituted on the phenyl by $C_1$–$C_4$alkyl; or $R_1$ is $C_1$–$C_8$acyl;

n is 1, 2, 3 or 4;

when n is 1, A is $C_1$–$C_{18}$alkyl, $C_3$–$C_6$alkenyl, $C_7$–$C_9$phenylalkyl which is unsubstituted or mono-, di- or tri-substituted on the phenyl by $C_1$–$C_4$alyl; or A is also one of the groups of the formulae (IIa)–(IIc)

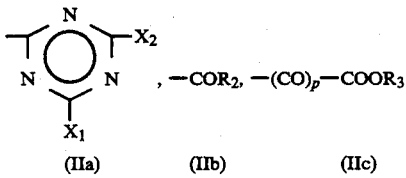, $-COR_2$, $-(CO)_p-COOR_3$

(IIa)     (IIb)     (IIc)

in which $X_1$ and $X_2$ which can be identified or different are a group $-OR_4$, $-SR_4$ or $$-\underset{\underset{R_5}{|}}{N}-R_6$$

where $R_4$, $R_5$ and $R_6$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl; $C_3$–$C_{18}$alkenyl, phenyl which is unsubstituted or mono-, di- or tri-substituted by $C_1$–$C_4$alkyl or $C_1$–$C_4$alkoxy; $C_7$–$C_9$phenylalkyl which is unsubstituted or mono-, di- or tri-substituted on the phenyl by $C_1$–$C_4$alkyl; $C_2$–$C_4$alkyl substituted in the 2-, 3- or 4-position by OH, by $C_1$–$C_8$alkoxy, by di($C_1$–$C_4$alkyl)amino or by 1-pyrrolidyl, 1-piperidyl, 4-morpholinyl, 4-methyl-1-piperazinyl or 1-hexahydroazepinyl; tetrahydrofurfuryl or a group of the formula (III)

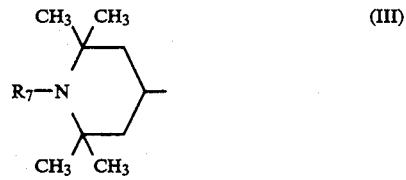

where $R_7$ is as defined for $R_1$; or

is 1-pyrrolidyl, 1-piperidyl, 4-morpholinyl, 4-methyl-1-piperazinyl or 1-hexahydroazepinyl; or $X_1$ and $X_2$ are one of the groups of the formulae (IVa)–(IVc)

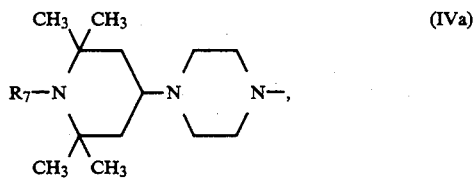

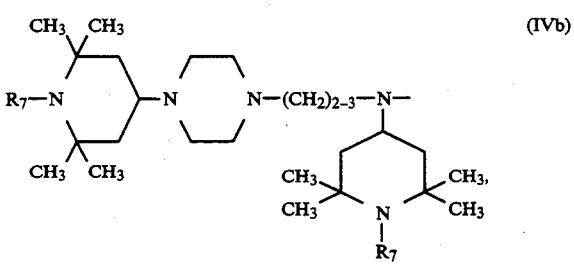

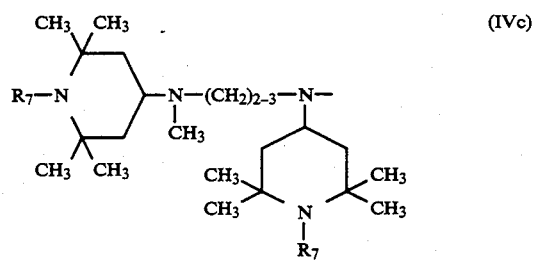

with $R_7$ being as defined above;

$R_2$ is hydrogen, $C_1$–$C_{18}$alkyl, $C_5$–$C_{12}$cycloalkyl which is unsubstituted or mono-, di- or tri-substituted by $C_1$–$C_4$alkyl; $C_2$–$C_{18}$alkenyl, phenyl which is unsubstituted or mono-, di- or tri-substituted by $C_1$–$C_4$alkyl or $C_1$–$C_4$alkoxy and/or monosubstituted by an OH group; $C_7$–$C_9$phenylalkyl which is unsubstituted or mono-, di- or tri-substituted on the phenyl by $C_1$–$C_4$alkyl and/or monosubstituted by an OH group;

p is zero or 1;

$R_3$ is $C_1$–$C_{18}$alkyl, $C_5$–$C_{12}$cycloalkyl which is unsubstituted or mono-, di- or tri-substituted by $C_1$–$C_4$alkyl; $C_3$–$C_{18}$alkenyl, $C_7$–$C_9$phenylalkyl which is unsubstituted or mono-, di- or tri-substituted on the phenyl by $C_1$–$C_4$alkyl; or a group of the formula (III);

when n is 2, A is $C_2$–$C_{12}$alkylene, $C_4$–$C_{12}$alkylene interrupted by 1, 2 or 3 oxygen atoms; 2-hydroxytrimethylene, phenylenedimethylene or one of the groups of the formulae (Va)–(Ve)

(Va), (Vb), (Vc) —CO—$R_8$—CO—,

—COO—$R_9$—OOC—, —(CH$_2$)$_q$—CO—
(Vd)         (Ve)

in which $X_3$ is as defined above for $X_1$ and $X_2$; or $X_3$ is a group of the formula (VI)

(VI)

with R 1 being as defined above;
$E_1$ is one of the groups of the formulae (VIIa)–(VIIc)

—$G_1$—$R_{10}$—$G_2$—,     (VIIa)

(VIIb) —($G_3$—$R_{11}$)$_r$—N   $G_4$—, (VIIc)

in which $G_1$, $G_2$ and $G_3$ which can be identical or different are —O— or

—N—$R_{14}$ where $R_{14}$ is hydrogen, $C_1$-$C_{18}$alkyl, $C_5$-$C_{12}$cycloalkyl which is unsubstituted or mono-, di- or tri-substituted by $C_1$-$C_4$alkyl; $C_7$-$C_9$phenylalkyl which is unsubstituted or mono-, di- or tri-substituted on the phenyl by $C_1$-$C_4$alkyl; or a group of the formula (III);
$R_{10}$ is $C_2$-$C_{12}$alkylene, $C_4$-$C_{12}$alkylene interrupted by 1, 2 or 3 oxygen atoms or by 1 or 2

—N—$R_{15}$ groups where R is as defined above for $R_{14}$ or is $C_1$-$C_8$acyl or ($C_1$-$C_8$alkoxy)carbonyl; $C_5$-$C_7$cycloalkylene, $C_5$-$C_7$cycloalkylenedi($C_1$-$C_4$alkylene), $C_1$-$C_4$alkylenedi($C_5$-$C_7$cycloalkylene), $C_2$-$C_4$alkylidenedi($C_5$-$C_7$cycloalkylene), phenylene, phenylenedi($C_1$-$C_4$alkylene), $C_1$-$C_4$alkylenediphenylene or $C_2$-$C_4$alkylidenediphenylene;
$R_{11}$ is $C_2$-$C_6$alkylene;
$G_4$ is one of the groups >N—($R_{11}$-$G_3$)$_s$—,- >CH—O— or

>CH—CH$_2$—N—
              |
              $R_{14}$ with $R_{14}$ being as defined above;
r and s which can be identical or different are zero or 1;
$R_{12}$ is hydrogen or, when r is 1 and $G_4$ is >CH—O—, $R_{12}$ is also methyl;
$R_{13}$ is hydrogen or methyl;
$R_8$ is a direct bond, $C_1$-$C_{12}$alkylene, $C_2$-$C_4$alkenylene, cyclohexylene, cyclohexenylene or phenylene;
$R_9$ is $C_2$-$C_{12}$alkylene, $C_4$-$C_{12}$alkylene interrupted by 1, 2 or 3 oxygen atoms;
$C_5$-$C_7$cycloalkylene, $C_5$-$C_7$cycloalkylenedi($C_1$-$C_4$alkylene) or
$C_2$-$C_4$ alkylidenedi($C_5$-$C_7$cycloalkylene);
q is zero or an integer from 1 to 10;
when n is 3, A is aliphatic $C_4$-$C_{18}$triacyl, aromatic $C_9$-$C_{18}$triacyl or a group of the formula (VIII)

(VIII)

in which $X_3$ is as defined above;
$E_2$ is one of the groups of the formulae (IXa)–(IXc)

—$G_5$—$R_{16}$—N—$R_{17}$—$G_6$—,  —N—(CH$_2$)$_u$—CH—(CH$_2$)$_v$—N—,
            |                    |           |            |
           ($R_{18}$)           $R_{19}$     $G_8$        $R_{20}$
            |                                |
            $G_7$                           N—$R_{21}$
            |)$_t$ (IXa)                              (IXb)

$R_{22}$—(O—)$_3$
(IXc)

in which $G_5$, $G_6$ and $G_7$ which can be identical or different are as defined above for $G_1$, $G_2$ and $G_3$;
$R_{16}$, $R_{17}$ and $R_{18}$ which can be identical or different are $C_2$-$C_6$alkylene;
t is zero or 1;
$R_{19}$, $R_{20}$ and $R_{21}$ which can be identical or different are as defined above for $R_{14}$;
$G_8$ is a direct bond or —CH$_2$—;
u and v which can be identical or different are integers from 2 to 6; and
$R_{22}$ is $C_3$-$C_{12}$alkanetriyl;
when n is 4, A is aliphatic $C_6$-$C_{18}$tetraacyl, aromatic C10-C18tetraacyl or a group of the formula (Xa) or (Xb)

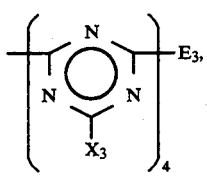

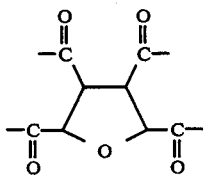

in which $X_3$ is as defined above;

$E_3$ is a group of the formulae (XIa)–(XIc)

 (XIa)

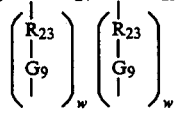

$R_{25}(-O)_4-$ (XIb)

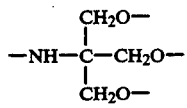 (XIc)

in which $G_9$ is as defined above for $G_1$, $G_2$ and $G_3$;

$R_{23}$ and $R_{24}$ which can be identical or different are $C_2-C_6$alkylene;

w is zero or 1; and $R_{25}$ is $C_4-C_{12}$alkanetetrayl.

Examples of alkyl having not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of OH-substituted $C_2-C_4$alkyl are 2-hydroxyethyl, 2-hydroxypropyl, 3-hydroxypropyl, 2-hydroxybutyl and 4-hydroxybutyl. 2-Hydroxyethyl is preferred.

Examples of $C_2-C_4$alkyl substituted by $C_1-C_8$alkoxy, preferably $C_1-C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2-C_4$alkyl substituted by di($C_1-C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Examples of $C_2-C_4$alkyl substituted by a 5- to 7-membered nitrogen-containing heterocyclic group are the groups of the formula

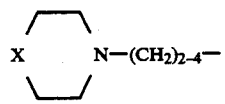

in which X is a direct bond, —O—, $CH_3N-$, (Xa)

—CH$_2$— or —CH$_2$CH$_2$—.

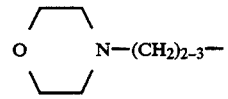 (Xb)

is preferred.

Examples of alkoxy having not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6-C_{12}$alkoxy, in particular heptoxy or octoxy, are preferred for $R_1$ and $R_7$.

Examples of unsubstituted or substituted $C_5-C_{12}$cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl; cyclohexyl which is unsubstituted or substituted by $C_1-C_4$alkyl is preferred.

Representative examples of $C_5-C_{12}$cycloalkoxy $R_1$ and $R_7$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having not more than 18 carbon atoms are vinyl, allyl, 2-methylallyl, butenyl, hexenyl, decenyl, undecenyl and oleyl.

Examples of substituted phenyl are methylphenyl, dimethylphenyl, trimethylphenyl, t-butylphenyl, di-t-butylphenyl, 3,5-di-t-butyl-4-methylphenyl, methoxyphenyl, ethoxyphenyl, hydroxyphenyl and 3,5-di-t-butyl-4-hydroxyphenyl.

Examples of phenylalkyl which is unsubstituted or substituted on the phenyl are benzyl, methylbenzyl, dimethylbenzyl, trimethylbenzyl, t-butylbenzyl, 2-phenylethyl and 2-( 3,5-di-t-butyl-4-hydroxyphenyl)ethyl.

Acyl having not more than 8 carbon atoms can be an aliphatic or aromatic group. Representative examples are formyl, acetyl, propionyl, butyryl, pentanoyl, hexanoyl, heptanoyl, octanoyl, benzoyl, acryloyl or crotonyl. $C_1-C_8$alkanoyl, $C_3-C_8$alkenoyl and benzoyl are preferred. Acetyl is especially preferred. The carbon atom in the 1-position is conveniently saturated in the acyl radical.

Representative examples of a 5- to 7-membered heterocyclic group

are 1-pyrrolidyl, 1-piperidyl, 4-morpholinyl, 4-methyl-1-piperazinyl and 1-hexahydroazepinyl. 4-Morpholinyl is preferred.

Examples of alkylene having not more than 12 carbon atoms are methylene, ethylene, propylene, trimethylene, tetramethylene, pentamethylene, 2,2-dimethyltrimethylene, hexamethylene, trimethylhexamethylene, decamethylene and dodecamethylene.

Examples of $C_4$–$C_{12}$alkylene interrupted by 1, 2 or 3 oxygen atoms are 3-oxapentane-1,5-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Preferred examples of $C_4$–$C_{12}$alkylene $R_{10}$ interrupted by 1 or 2

groups are the groups

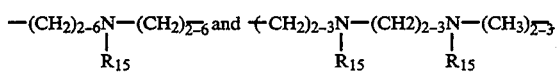

Representative examples of groups containing 1 or 2 $C_5$–$C_7$cycloalkylene groups are cyclohexylene, methylcyclohexylene, cyclohexylenedimethylene, methylenedicyclohexylene and isopropylidenedicyclohexylene.

Representative examples of groups containing 1 or 2 phenylene groups are phenylene, methylphenylene, dimethylphenylene, phenylenedimethylene, methylenediphenylene and isopropylidenediphenylene.

Examples of $C_2$–$C_4$alkenylene are vinylene, methylvinylene and dimethylvinylene.

Aliphatic $C_4$–$C_{18}$triacyl A can be unsubstituted or substituted by an OH group. Preferred examples are the triacyls derived from methanetricarboxylic, 1,1,2-ethanetricarboxylic, 1,2,3-propanetricarboxylic, citric or 1,2,3-butanetricarboxylic acids.

Aromatic $C_9$–$C_{18}$triacyl A is, for example, a triacyl derived from 1,2,4-benzenetricarboxylic or 1,3,5-benzenetricarboxylic acid.

Preferred examples of $C_3$–$C_{12}$alkanetriyl $R_{22}$ are 1,2,3-propanetriyl, 1,2,4-butanetriyl, 1,2,6-hexanetriyl or a group

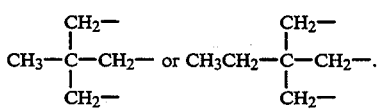

Aliphatic $C_6$–$C_{18}$tetraacyl A is, for example, a tetraacyl derived from 1,1,3,3-propanetetracarboxylic acid or from 1,2,3,4-butanetetracarboxylic acid.

Aromatic $C_{10}$–$C_{18}$tetraacyl A is, for example, a tetraacyl derived from 1,2,4,5-benzenetetracarboxylic acid.

Preferred examples of $C_4$–$C_{12}$alkanetetrayl $R_{25}$ are 1,2,3,4-butanetetrayl and the group

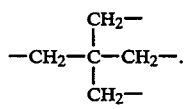

($C_1$–$C_8$alkoxy)carbonyl is for example methoxycarbonyl, ethoxycarbonyl, propoxycarbonyl, butoxycarbonyl, pentoxycarbonyl, hexoxycarbonyl, heptoxycarbonyl and octoxycarbonyl.

The preferred definitions of $R_1$ and $R_7$ are hydrogen, $C_1$–$C_4$alkyl, OH, $C_6$–$C_{12}$alkoxy, $C_5$–$C_8$cycloalkoxy, allyl, benzyl or acetyl, in particular hydrogen or methyl.

Those compounds of the formula (I) are preferred in which n is 1, 2, 3 or 4 and, when n is 1, A is $C_1$–$C_{18}$alkyl, $C_3$–$C_4$alkenyl, benzyl which is unsubstituted or mono-, di- or tri-substituted on the phenyl by $C_1$–$C_4$alkyl; or A is one of the groups of the formulae (IIa)–(IIc) in which $X_1$ and $X_2$ which can be identical or different are a group —$OR_4$, —$SR_4$ or

where $R_4$, $R_5$ and $R_6$ which can be identical or different are hydrogen, $C_1$–$C_{18}$alkyl, $C_5$–$C_8$cycloalkyl which is unsubstituted or mono-, di- or tri-substituted by $C_1$–$C_4$alkyl; $C_3$–$C_{18}$alkenyl, phenyl which is unsubstituted or mono-, di- or tri-substituted by $C_1$–$C_4$alkyl or $C_1$–$C_4$alkoxy; benzyl which is unsubstituted or mono-, di- or tri-substituted on the phenyl by $C_1$–$C_4$alkyl; $C_2$–$C_3$alkyl substituted in the 2- or 3-position by OH, by $C_1$–$C_4$alkoxy, by di($C_1$–$C_4$alkyl)amino or by a group

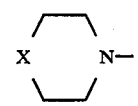

where X is a direct bond, —O—, —$CH_2$— or —$CH_2CH_2$—; tetrahydrofurfuryl or a group of the formula (III), or the group

is a group

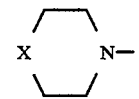

as defined above, or $X_1$ and $X_2$ are one of the groups of the formulae (IVa)–(IVc), $R_2$ is hydrogen, $C_1$–$C_{17}$alkyl, $C_5$–$C_8$cycloalkyl which is unsubstituted or mono-, di- or tri-substituted by $C_1$–$C_4$alkyl; $C_2$–$C_{17}$alkenyl, phenyl which is unsubstituted or mono-, di- or tri-substituted by $C_1$–$C_4$alkyl or $C_1$–$C_4$alkoxy and/or monosubstituted by an OH group; benzyl or phenylethyl which, both, are unsubstituted or mono-, di- or tri-substituted on the phenyl by $C_1$–$C_4$alkyl and/or monosubstituted by an OH group; p is zero or 1, $R_3$ is $C_1$–$C_{18}$alkyl, $C_5$–$C_8$cycloalkyl which is unsubstituted or mono-, di- or tri-substituted by $C_1$–$C_4$alkyl; $C_3$–$C_{18}$alkenyl, benzyl which is unsubstituted or mono-, di- or tri-substituted on the phenyl by $C_1$–$C_4$alkyl; or a group of the formula (III), and, when n is 2, A is $C_2$–$C_{10}$alkylene, $C_4$–$C_{10}$alkylene interrupted by 1, 2 or 3 oxygen atoms; 2-hydroxytrimethylene, phenylenedimethylene or one of the groups of the formulae (Va)–(Ve) in which $X_3$ is as defined above for $X_1$ and $X_2$ or is a group of the formula (VI), $E_1$ is one of the groups of the formulae (VIIa)–(VIIc) in which $G_1$, $G_2$ and $G_3$ which can be identical or different are —O— or

where $R_{14}$ is hydrogen, $C_1$–$C_{18}$alkyl, $C_5$–$C_8$cycloalkyl which is unsubstituted or mono-, di- or tri-substituted by $C_1$–$C_4$alkyl; benzyl which is unsubstituted or mono-, di- or tri-substituted on the phenyl by $C_1$–$C_4$alkyl; or a group of the formula (III), $R_{10}$ is $C_2$–$C_{10}$alkylene, $C_4$–$C_{10}$alkylene interrupted by 1, 2 or 3 oxygen atoms or by 1 or 2

groups where $R_{15}$ is as defined above for $R_{14}$ or is $C_1$–$C_6$acyl or $(C_1$–$C_6$alkoxy$)$carbonyl; cyclohexylene, cyclohexylenedimethylene, methylenedicyclohexylene, isopropylidenedicyclohexylene, phenylene, phenylenedimethylene, methylenediphenylene, or isopropylidenediphenylene, $R_{11}$ is $C_2$–$C_4$alkylene, $G_4$ is $>N$—$(R_{11}$–$G_3)_s$—,

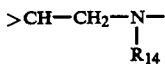

with $R_{14}$ being as defined above, r and s which an be identical or different are zero or 1; $R_{12}$ is hydrogen or, when r is 1 and $G_4$ is $>CH$—$O$—, is also methyl; and $R_{13}$ is hydrogen or methyl, $R_8$ is a direct bond, $C_1$–$C_{10}$alkylene, vinylene, cyclohexylene or phenylene, $R_9$ is $C_2$–$C_{10}$alkylene, $C_4$–$C_{10}$alkylene interrupted by 1, 2 or 3 oxygen atoms; cyclohexylene, cyclohexylenedimethylene or isopropylidenedicyclohexylene and q is zero or an integer from 1 to 5, and, when n is 3, A is aliphatic $C_4$–$C_{12}$triacyl, aromatic $C_9$–$C_{12}$triacyl or a group of the formula (VIII) in which $X_3$ is as defined above and $E_2$ is one of the groups of the formulae (IXa)–(IXc) in which $G_5$, $G_6$ and $G_7$ which can be identical or different are as defined above for $G_1$, $G_2$ and $G_3$; $R_{16}$, $R_{17}$ and $R_{18}$ which can be identical or different are $C_2$–$C_6$alkylene, t is zero or 1, $R_{19}$, $R_{20}$ and $R_{21}$ which can be identical or different are as defined above for $R_{14}$; $G_8$ is a direct bond or —$CH_2$—, u and v which can be identical or different are integers from 2 to 6 and $R_{22}$ is $C_3$–$C_{10}$alkanetriyl, and, when n is 4, A is aliphatic $C_6$–$C_{12}$tetraacyl, aromatic $C_{10}$–$C_{12}$tetraacyl or a group of the formula (Xa) or (Xb) in which $X_3$ is as defined above and $E_3$ is a group of the formula (XIa)–(XIc) in which $G_9$ is as defined above for $G_1$, $G_2$ and $G_3$; $R_{23}$ and $R_{24}$ which can be identical or different are $C_2$–$C_6$alkylene, w is zero or 1 and $R_{25}$ is $C_4$–$C_8$alkanetetrayl.

Those compounds of the formula (I) are particularly preferred in which n is 1, 2, 3 or 4 and, when n is 1, A is methyl, $C_4$–$C_{18}$alkyl, allyl, benzyl or one of the groups of the formulae (IIa)–(IIc) in which $X_1$ and $X_2$ which can be identical or different are a group —$OR_4$, —$SR_4$ or

where $R_4$, $R_5$ and $R_6$ which can be identical or different are hydrogen, $C_1$–$C_{12}$alkyl, cyclohexyl which is unsubstituted or mono-, di- or tri-substituted by $C_1$–$C_4$alkyl; allyl, undecenyl, phenyl, benzyl, $C_2$–$C_3$alkyl substituted in the 2- or 3-position by OH, by $C_1$–$C_4$alkoxy, by dimethylamino, by diethylamino or by 4-morpholinyl; tetrahydrofurfuryl or a group of the formula (III), or the group

is 4-morpholinyl, or $X_1$ and $X_2$ are one of the groups of the formulae (IVa)–(IVc), $R_2$ is $C_2$–$C_{17}$alkyl, cyclohexyl which is unsubstituted or mono-, di- or tri-substituted by $C_1$–$C_4$alkyl; $C_2$–$C_{10}$alkenyl, phenyl, t-butylphenyl, 3,5-di-t-butyl-4-hydroxyphenyl, benzyl or 2-(3,5-di-t-butyl-4-hydroxyphenyl)-ethyl, p is zero or 1, $R_3$ is $C_2$–$C_{18}$alkyl, cyclohexyl which is unsubstituted or mono-, di- or tri-substituted by $C_1$–$C_4$alkyl; allyl, undecenyl, oleyl, benzyl or a group of the formula (III), and, when n is 2, A is $C_2$–$C_8$alkylene, $C_4$–$C_8$alkylene interrupted by 1 or 2 oxygen atoms; 2-hydroxytrimethylene, phenylenedimethylene or one of the groups of the formulae (Va)–(Ve) in which $X_3$ is as defined above for $X_1$ and $X_2$ or is a group of the formula (VI), $E_1$ is one of the groups of the formulae (VIIa)–(VIIc) in which $G_1$, $G_2$ and $G_3$ which can be identical or different are —O— or

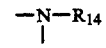

where $R_{14}$ is hydrogen, $C_1$–$C_{12}$alkyl, cyclohexyl which is unsubstituted or mono-, di- or tri-substituted by $C_1$–$C_4$alkyl; benzyl or a group of the formula (III), $R_{10}$ is $C_2$–$C_8$alkylene, $C_4$–$C_{10}$alkylene interrupted by 1, 2 or 3 oxygen atoms or by 1 or 2

groups where $R_{15}$ is as defined above for $R_{14}$ or is $C_1$–$C_4$acyl or $(C_1$–$C_4$alkoxy$)$carbonyl; cyclohexylenedimethylene, methylenedicyclohexylene, isopropylidenedicyclohexylene, phenylenedimethylene or isopropylidenediphenylene, $R_{11}$ is $C_2$–$C_3$alkylene, $G_4$ is $>N$—$(R_{11}$–$G_3)_s$— or $>CH$—$O$—, r and s which can be identical or different are zero or 1; $R_{12}$ is hydrogen or, when r is 1 and $G_4$ is $>CH$—$O$—, is also methyl; and $R_{13}$ is hydrogen or methyl, $R_8$ is a direct bond or $C_1$–$C_8$alkylene, $R_9$ is $C_2$–$C_8$alkylene, $C_4$–$C_8$alkylene interrupted by 1 or 2 oxygen atoms; cyclohexylenedimethylene or isopropylidenedicyclohexylene and q is zero or an integer from 1 to 3 and, when n is 3, A is aliphatic $C_4$–$C_8$triacyl, benzenetricarbonyl or a group of the formula (VIII) in which $X_3$ is as defined above and $E_2$ is one of the groups of the formulae (IXa)–(IXc) in which $G_5$, $G_6$ and $G_7$ which can be identical or different are as defined above for $G_1$, $G_2$ and $G_3$; $R_{16}$, $R_{17}$ and $R_{18}$ which can be identical or different are $C_2$–$C_4$alkylene, t is zero or 1, $R_{19}$, $R_{20}$ and $R_{21}$ which can be identical or different are as defined above for $R_{14}$; $G_8$ is a direct bond or —$CH_2$—, u and v which can be identical or different are integers from 3 to 6 and $R_{22}$ is $C_3$–$C_6$alkanetriyl, and, when n is 4, A is aliphatic $C_6$–$C_8$tetraacyl, benzenetetracarbonyl or a group of the formula (Xa) or (Xb) in which $X_3$ is as defined above and $E_3$ is a group of the formulae (XIa)-(XIc) in which $G_9$ is as defined above for $G_1$, $G_2$ and $G_3$; $R_{23}$ and $R_{24}$ which can be identical or different are $C_2$–$C_4$alkylene, w is zero or 1 and $R_{25}$ is $C_4$–$C_6$alkanetetrayl.

Those compounds of the formula (I) are of special interest in which n is 1, 2, 3 or 4 and, when n is 1, A is methyl, $C_8$–$C_{18}$alkyl or one of the groups of the formulae (IIa)-(IIc) in which $X_1$ and $X_2$ which can be identical or different are a group —OR$_4$ or

where $R_4$ is $C_1$–$C_8$alkyl or a group of the formula (III), $R_5$ and $R_6$ which can be identical or different are $C_1$–$C_8$alkyl, cyclohexyl, $C_2$–$C_3$alkyl substituted in the 2- or 3-position by methoxy, by ethoxy, by dimethylamino, by diethylamino or by 4-morpholinyl; tetrahydrofurfuryl or a group of the formula (III) or $R_5$ is also hydrogen or the group

4-morpholinyl, $R_2$ is $C_3$–$C_{17}$alkyl, cyclohexyl, phenyl, 3,5-di-t-butyl-4-hydroxyphenyl or 2-(3,5-di-t-butyl-4-hydroxyphenyl)-ethyl, p is zero, $R_3$ is $C_4$–$C_{18}$alkyl, cyclohexyl, t-butylcyclohexyl or a group of the formula (II), and, when n is 2, A is one of the groups of the formulae (Va)-(Ve) in which $X_3$ is as defined above for $X_1$ and $X_2$ or is a group of the formula (VI), $E_1$ is one of the groups of the formulae (VIIa)-(VIIc) in which $G_1$ and $G_2$ which can be identical or different are —O— or

where $R_{14}$ is hydrogen, $C_1$–$C_8$alkyl, cyclohexyl or a group of the formula (III), $R_{10}$ is $C_2$–$C_6$alkylene, $C_6$–$C_{10}$alkylene interrupted by 2 or 3 oxygen atoms; cyclohexylenedimethylene or methylenedicyclohexylene, the group (VIIb) is one of the groups

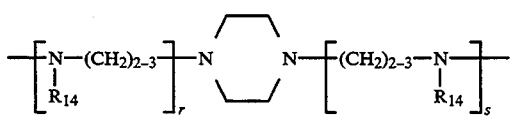

and

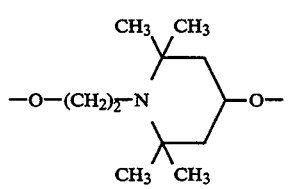

where r and s which can be identical or different are zero or 1, $R_{14}$ is as defined above, and $R_{13}$ is hydrogen or methyl, $R_8$ is $C_2$–$C_8$alkylene, $R_9$ is $C_4$–$C_8$alkylene or isopropylidenedicyclohexylene and q is zero or 1, and, when n is 3, A is a group of the formula (VIII) in which $X_3$ is as defined above and $E_2$ is a group of the formula (IXa) or (IXb) in which $G_5$ and $G_6$ which can be identical or different are as defined above for $G_1$ and $G_2$; $R_{16}$ and $R_{17}$ which can be identical or different are $C_2$–$C_3$alkylene, t is zero, $R_{19}$, $R_{20}$ and $R_{21}$ are as defined above for $R_{14}$; $G_8$ is a direct bond or —CH$_2$— and u and v which can be identical or different are integers from 3 to 5, and, when n is 4, A is a group of the formula (Xa) in which $X_3$ is as defined above and $E_3$ is a group of the formula (XIa) in which $G_9$ is as defined above for $G_1$ and $G_2$; $R_{23}$ and $R_{24}$ which can be identical or different are $C_2$–$C_3$alkylene and w is zero or 1.

Those compounds of the formula (I) are of particular interest in which $R_1$ is hydrogen or methyl, n is 1, 2, 3 or 4 and, when n is 1, A is methyl or one of the groups of the formulae (IIa)-(IIc) in which $X_1$ and $X_2$ which can be identical or different are a group —OR$_4$ or

where $R_4$ is $C_1$–$C_4$alkyl, 2,2,6,6-tetramethyl-4-piperidyl or 1,2,2,6,6-pentamethyl-4-piperidyl, $R_5$ and $R_6$ which can be identical or different are $C_1$–$C_4$alkyl, cyclohexyl, tetrahydrofurfuryl, 2,2,6,6-tetramethyl-4-piperidyl or 1,2,2,6,6opentamethyl-4-piperidyl or $R_5$ is also hydrogen or the group

is 4-morpholinyl, $R_2$ is $C_5$–$C_{17}$alkyl, p is zero and $R_3$ is $C_6$–$C_{18}$alkyl, and, when n is 2, A is one of the groups of the formulae (Va)-(Vd) in which $X_3$ is as defined above for $X_1$ and $X_2$ or is a group of the formula (VI), $E_1$ is a group

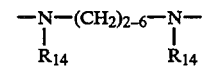

where $R_{14}$ is hydrogen, methyl, 2,2,6,6-tetramethyl-4-piperidyl or 1,2,2,6,6-pentamethyl-4-piperidyl, $R_8$ is $C_4$–$C_8$ alkylene and $R_9$ is $C_4$–$C_6$alkylene, and, when n is 3, A is a group of the formula (VIII) in which $X_3$ is as defined above and $E_2$ is a group

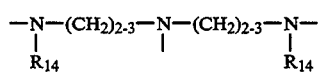

where $R_{14}$ is as defined above, and, when n is 4, A is a group of the formula (Xa) in which $X_3$ is as defined above and $E_3$ is a group

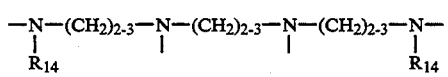

with $R_{14}$ being as defined above.

Those compounds of the formula (I) are also of interest in which $R_1$ is hydrogen or methyl, n is 1, 2, 3 or 4 and, when n is 1, A is methyl or a group of the formula (IIb) in which $R_2$ is $C_5$–$C_{17}$alkyl, and, when n is 2, A is a group of the formula (Va) or (Vb), in which X₃ is a group of the formula (VI) and E₁ is a group

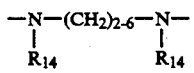

where R₁₄ is 2,2,6,6-tetramethyl-4-piperidyl or 1,2,2,6,6-pentamethyl-4-piperidyl, and, when n is 3, A is a group of the formula (VIII) in which X₃ is as defined above and E₂ is a group

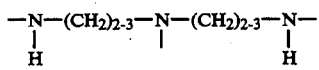

and, when n is 4, A is a group of the formula (Xa) in which X₃ is as defined above and E₃ is a group

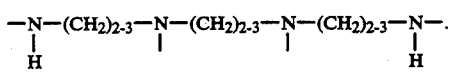

The compounds of the formula (I) can be prepared by processes known per se, e.g. by reacting N,1-bis(2,2,6,6-tetramethyl-4-piperidyl)-4-piperidinemethanamine of the formula

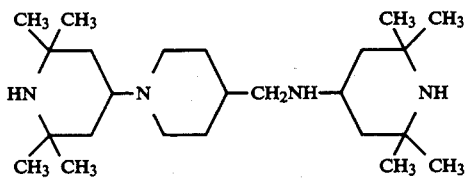

with suitable alkylating or acylating reagents in the appropriate molar ratios.

In this way, the compounds of the formula (I) with R₁=H are obtained, from which the corresponding compounds with R₁≠H can subsequently be obtained.

The reactions are conveniently carried out in an inert solvent, operating at temperatures from e.g. −20° to 200° C., preferably from −10° to 180° C.

The N,1-bis(2,2,6,6-tetramethyl-4-piperidyl)-4-piperidinemethanamine can be prepared, for example, according to scheme 1, by reacting 2 mol of 2,2,6,6-tetramethyl-4-piperidone with 1 mol of 4-piperidinemethanamine in order to obtain an enamine-ketimine of the formula (XII) which is then hydrogenated in the presence of a hydrogenation catalyst such as platinum, palladium or nickel.

Scheme 1

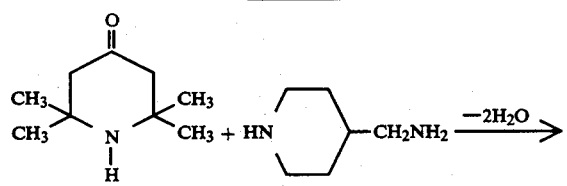

-continued
Scheme 1

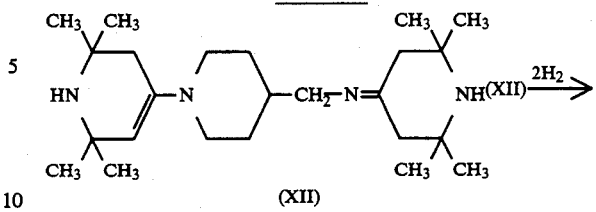

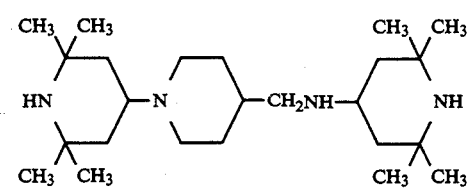

The reactions according to scheme 1 are preferably carried out in the same reactor. The enamine-ketimine of the formula (XII) can be prepared without solvent or in the presence of a hydrocarbon solvent having a boiling point between e.g. 60° and 180° C., preferably between 80° and 140° C., if appropriate in the presence of an organic acid or inorganic acid, for example benzoic or sulfuric acid; the hydrogenation is preferably carried out in the presence of a C₁-C₄alkanol.

The reagents used are commercially available and can be prepared by known processes.

As mentioned at the outset, the compounds of the formula (I) are highly effective in improving the light stability, heat stability and oxidation stability of organic materials, in particular synthetic polymers and copolymers.

Examples of such organic materials which can be stabilised are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

2. Mixtures of the polymers mentioned under 1 ), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate copolymers and their copolymers with carbon monoxide or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1 ) above, for example polypropylene/ethylene-propylene-copolymers, LDPE/ethylene-vinyl acetate copolymers (EVA), LDPE/ethylene-acrylic acid copolymers (EAA), LLDPE/EVA, LLDPE/EAA and statistical or alternating polyalkylene/carbon monoxide-copolymers as well as their mixtures with other polymers, for example polyamide.

3a. Hydrocarbon resins (for example C5–C9) and hydrogenated modifications thereof (for example tackyfiers) and mixtures of polyalkylenes and starch.

4. Polystyrene, poly-(p-methylstyrcnc), poly-(α-methylstyrene).

5. Copolymers of styrene or α-methylstyrene with dienes or acrylic derivatives, such as, for example, styrene/butadiene, styrene/acrylonitrile, styrene/alkyl methacrylate, styrene/maleic anhydride, styrene/-butadiene/alkyl acrylate, styrene/butadiene/alkyl methacrylate styrene/acrylonitrile/methyl acrylate; mixtures of high impact strength from styrene copolymers and another polymer, such as, for example, from a polyacrylate, a diene polymer or an ethylene/-propylene/diene terpolymer; and block copolymers of styrene, such as, for example, styrene/butadiene/styrene, styrene/isoprene/styrene, styrene/ethylene/-butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybumdiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, copolymers of ethylene and chlorinated ethylene, epichlorohydrin homo- and co-polymers, polymers from halogen-containing vinyl compounds, as for example, poly-vinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, with butyl acrylate impact resistant modified polymethyl methacrylate, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylatcs or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corre- sponding lactams, such as polyamide 4, polyamide 6, polyamide 6/6, 6/10, 6/9, 6/12, 4/6, 12/12 polyamide 11, polyamide 12, aromatic polyamides obtained by condensation of m-xylene diamine and adipic acid; polyamides prepared from hexamethylenediamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which am derived from dicarboxylic acids and diols andl[ch]or from hydroxycarboxylic acids or the corresponding lactones, such as polyethylene terephthalate, polybutylene terephthalate, poly-1,4-dimethylolcyclohexane terephthalate, poly-[2,2,-(4-hydroxyphenyl)- propane] terephthalate and polyhydroxybenzoates as well as block-copolyether-esters derived from polyethers having hydroxyl end groups.

18. Polycarbonates and polyester-carbonates.

19. Polysulfones, polyether-sulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilised, on the end use and on the presence of other additives.

In general, it is appropriate to use, for example, 0.01 to 5% by weight of the compounds of the formula (I), relative to the weight of the material to be stabilised, preferably between 0.05 and 1%.

In general, the compounds of the formula (I) can be incorporated in the polymeric materials before, during or after the polymerization or crosslinking of the said materials.

The compounds of the formula (I) can be incorporated in the polymeric materials in the pure form or encapsulated in waxes, oils or polymers.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilised with the products of the formula (I) can be used for the production of mouldings, films, tapes, monofilaments, fibres, surface coatings and the like.

If desired, other conventional additives for synthetic polymers, such as antioxidants, UV absorbers, nickel stabilisers, pigments, fillers, plasticisers, antistatic agents, flameproofing agents, lubricants, corrosion inhibitors and metal deactivators, can be added to the mixtures of the compounds of the formula (I) with the organic materials.

Particular examples of additives which can be used in admixture with the compounds of the formula (I) are:

1. Antioxidants 1.1. Alkylated monophenols, for example 2,6-di-tert-butyl-4-methyl-phenol, 2-tert-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methyl-undec-1'-yl)-phenol, 2,4-dimethyl-6-( 1'-methyl-heptadec-1'-yl)-phenol, 2,4-dimethyl-6-(1'-methyl-tridec-1'-yl)-phenol and mixtures therof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-di-phenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxy-phenyl-stearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thio-bis-(3,6-di-sec-amylphenol), 4,4'-bis-(2,6-dimethyl-4-hydroxyphenyl)-disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,60 -dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butan, 2,2-bis-(3,5-di-tert.-butyl-4-hydroxyphenyl)-propan, 2,2-bis-(5-tert.-butyl-4-hydroxy-2-methylphenyl)-4-n-dodecylmercapto-butan, 1,1,5,5-tetra-( 5-tert.-butyl-4-hydroxy-2-methylphenyl)-pentan.

1.6. O-, N- and S-benzyl compounds, for example 3,5,3',5'-tetra-tert.-butyl-4,4'-dihydroxydibenzylether, octadecyl-4-hydroxy-3,5-dimethylbenzylmercaptoacetate, tris-(3,5-di-tert.-butyl-4-hydroxybenzyl)-amine, bis-(4-tert.-butyl-3-hydroxy-2,6- dimethylbenzyl)dithioterephthalate, bis-( 3,5-di-tert.-butyl-4-hydroxybenzyl)-sulfide, isooctyl-3,5-di-tert.-butyl-4-hydroxybenzyl-mercaptoacetate.

1.7. Hydroxybenzylated Malonates, for example di-octadecyl-2,2-bis-(3,5-di-tert.-butyl-2-hydroxybenzyl)-malonate, di-octadecyl-2-(3-tert.-butyl-4-hydroxy-5-methylbenzyl)-malonate, di-dodecyl-mercaptoethyl-2,2-bis(3,5-di-tert.-butyl-4-hydroxybenzyl)-malonate, Di-[4-( 1,1,3,3-tetramethylbutyl)-phenyl]-2,2-bis-(3,5-di-tert.-butyl-4-hydroxybenzyl)-malonate.

1.8. Hydroxybenzyl-Aromatics, for example 1,3,5-tris-(3,5-di-tert.-butyl-4-hydroxy-benzyl)-2,4,6-trimethylbenzene, 1,4-bis-(3,5-di-tert.-butyl-4-hydroxybenzyl)-2,3,5,6-tetramethylbenzene, 2,4,6-tris-(3,5-di-tert.-butyl-4-hydroxybenzyl)-phenol.

1.9. Triazine Compounds, for example 2,4-bis-octyl-mercapto-6-(3,5-di-tert.-butyl-4-hydroxyanilino)-1,3,5-triazine, 2-octylmercapto-4,6-bis-(3,5-di-tert.-butyl-4-hydroxyanilino)- 1,3,5-triazine, 2-octylmercapto-4,6-bis-(3,5-di-tert.-butyl-4-hydroxyphenoxy) - 1,3,5-triazine, 2,4,6-tris-(3,5-di-tert.-butyl-4-hydroxyphenoxy)- 1,2,3-triazine, 1,3,5-tris-(3,5-di-tert.-butyl-4-hydroxybenzyl)-isocyanurate, 1,3,5-tris-(4-tert.-butyl-3-hydroxy-2,6-di-methylbenzyl)-isocyanurate, 2,4,6-tris-(3,5-di-tert.-butyl-4-hydroxyphenylethyl)-1,3,5-triazine, 1,3,5-tris-(3,5-di-tert.-butyl-4-hydroxyphenylpropionyl)-hexahydro-1,3,5-triazine, 1,3,5-tris-(3,5-dicyclohexyl-4-hydroxybenzyl)-isocyanurate.

1.10. Benzylphosphonates, for example dimethyl-2,5-di-tert.-butyl-4-hydroxybenzylphosphonate, diethyl-3,5-di-tert.-butyl-4-hydroxybenzylphosphonate, dioctadecyl-3,5-di-tert.-butyl-4-hydroxybenzylphosphonate, dioctadecyl-5-tert.-butyl-4-hydroxy-3-methylbenzylphosphonate, Ca-salt of the 3,5-di-tert.-butyl-4-hydroxybenzyl-phosphonic acid monoethylester.

1.11. Acylaminophenols, for example lauric acid 4-hydroxyanilide, stearic acid 4-hydroxyanilide, octyl N-(3,5-di-tert-butyl-4-hydroxyphenyl)-carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.15 Esters of 3,5-di-tert.-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.16. Amides of 13-(3,5-di-tert-butyl-4-hydroxyphenyl)propionic acid e.g. N,N'-bis(3,5- di-tert-butyl-4-hydroxyphenylpropionyl)hexamethylenediamine, N,N'-bis(3,5-di-tert-butyl-4-hydroxyphenylpropionyl)tri-methylene-diamine, N,N'-bis(3,5-di-tert-butyl-4-hydroxyphenylpropionyl)-hydrazine.

2. UV absorbers and light stabilisers 2.1.2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α- dimethylbenzyl), mixture of 5-chloro-3'-tert.-butyl-5'-(2-octyloxycarbonyl-ethyl)- and 5-chloro-3'-tert.-butyl-5'-[2-(2-ethylhexyloxy)-carbonylethyl]-, 5-chloro-3'-tert.-butyl-5'-(2-methoxycarbonylethyl)-, 3'-tert.-butyl-5'-(2-methoxycarbonylethyl)-, 3'-tert.-butyl-5'-(2-octyloxycarbonylethyl)-, 3'-tert.-butyl-5'-[2-(2-ethylhexyloxy)-carbonylethyl]-, 3'-dodecyl-5'-methyl- and 3'-tert.-butyl-5'-(2-isooctyloxycarbonylethyl)-2'-hydroxyphenyl-2H-benztriazole(2), 2,2'-methylene-bis[4-( 1,1,3,3-tetramethylbutyl)-6-benztriazole-2-ylphenol]; product of ester interchange of 2-[3'-tert.-butyl-5'-( 2-methoxycarbonylethyl)-2'-hydroxyphenyl]-2H-benztriazole with polyethylene glycol 300; [R-CH₂CH₂—COO(CH₂)₃]₂ with R=3'-tert.-butyl-4'-hydroxy-5'-2H-benzotriazole-2-yl-phenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tert.butylphenyl salicylate, phenyl salicylate, octylphenyl salicylate, dibenzoylresorcinol, bis-(4-tert.butylbenzoyl)-resorcinol, benzoylresorcinol, 2,4-di-tert.butylphenyl 3,5-di-tert.butyl-4-hydroxybenzoate, hexadecyl 3,5-di-tert. butyl-4-hydroxybenzoate, octadecyl 3,5-di-tert.-butyl-4-hydroxybenzoate, 2 methyl-4,6-di-tert.-butylphenyl 3,5-di-tert.-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)-phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methyl-phenyl undecyl ketoxime, nickel complexes of 1-phenyl-4-lauroyl-5-hydroxypyrazole, with or without additional ligands.

2.6. Sterically hindered amines, for example bis(2,2,6,6-tetramethyl-piperidyl) sebacate, bis-(2,2,6,6-tetramethyl-piperidyl) succinate, bis(1,2,2,6,6-pentamethylpiperidyl) sebacate, bis(1,2,2,6,6-pentamethylpiperidyl) n-butyl-3,5-di-tert-butyl-4-hydroxy-benzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis-(1,2,2,6,6-pentamethylpiperidyl)-2-n-butyl-2-(2-hydroxy-3,5-di-tert.-butylbenzyl) malonate, 3-n-octyl-7,7,9,9-tetramethyl- 1,3,8-triazasprio[4.5]decan-2,4-dion, bis-(1-octyloxy-2,2,6,6-tetramethyl-piperidyl) sebacate, his-( 1-octyloxy-2,2,6,6-tetramethylpiperidyl) succinate, product of condensation of N,N'-bis-(2,2,6,6-tetramethyl4-piperidyl)-hexamethylene diamine and 4-morpholino-2,6-dichloro-1,3,5-triazine, product of condensation of chloro-4,6-di-(4-n-butylamino-2,2,6,6-tetramethyl-piperidyl)-1,3,5-triazine and 1,2-bis-(3-aminopropylamino)ethane, product of condensation of 2-chloro-4,6-di-(4-n-butylamino- 1,2,2,6,6-pentamethylpiperidyl)- 1,3,5-triazine and 1,2-bis-(3-aminopropylamino)ethane, 8-acetyl-3-dodecyl-7,7,9,9-tetramethyl- 1,3,8-triazaspiro[4.5]decane-2,4-dion, 3-dodecyl- 1-(2,2,6,6-tetramethyl-4-piperidyl)pyrrolidin2,5-dion, 3-dodecyl- 1-( 1,2,2,6,6-pentamethyl-4-piperidyl)-pyrrolidin-2,5-dion.

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylamino-propyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8.2-(2-Hydroxyphenyl)-1,3,5-triazines, for example 2,4,6-tris(2-hydroxy-4-octyloxy-phenyl)-1,3,5-triazine, 2-(2-hydroxy-4-octyloxy-phenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)- 1,3,5-triazine, 2-(2-hydroxy-4-octyloxyphenyl)-4,6-bis(4-methylphenyl)-1,3,5-triazine, 2-(2-hydroxy-4-dodecyloxyphenyl )-4,6-bis(2,4-dimethylphenyl)-1,3,5-triazine, 2-[2-hydroxy-4-(2-hydroxy-3-butyloxy-propyloxy)-phenyl]-4,6-bis(2,4-dimethyl)-1,3,5-triazine, 2-[2-hydroxy-4-(2-hydroxy-3-octyloxy-propyloxy)-phenyl]-4,6-bis(2,4-dimethyl)- 1,3,5-triazin 3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4hydroxyphenylpropionyl)hydrazine, 3-salicyloylamino-1,2,4-triazole, bis(benzylidene)oxalodihydrazide, Oxanilide, isophthalic acid dihydrazide, sebacic acid-bis-phenylhydrazide, N,N'-diacetal-adipinic acid dihydrazide, N,N'-bis-salicyloyl-oxalic acid dihydrazide, N,N'-bis-salicyloyl-thiopropionic acid dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diiso- decyl pentaerythritol diphosphite, bis(2,4-di-tert.-butylphenyl) pentaerythritol diphosphite, bis-(2,6-di-tert.-butyl-4-methylphenyl)-pentaerythritol diphosphite, bis-isodecyloxy-pentaerythritol diphosphite, bis-(2,4-di-tert.-butyl-6-methylphenyl)-pentaerythritol diphosphite, bis-(2,4,6-tri-tert.-butylphenyl)-pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert.-butyl- 12H-dibenz[d,g]-1,3,2-dioxaphosphocin, 6-fluoro-2,4,8, 10-tetra-tert.-butyl- 12-methyl-dibenz[d,g]-1,3,2-dioxaphosphocin.

4a. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis(1-hydroxy-2,2,6,6-tetramethyl-4-piperidyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(p-dodecyl-mercapto )propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg behenate, Mg stearate, Na ricinoleate and K palmirate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The compounds of the formula (I) can also be used as stabilisers, especially as light stabilisers, for almost all materials known in the art of photographic reproduction and other reproduction techniques as e.g. described in Research Disclosure 1990, 31429 (pages 474 to 480).

Several examples of the preparation and use of the compounds of the formula (I) are reported for more detailed illustration of the present invention; these examples are given solely for illustrative purposes and do not imply any restriction.

The compounds of Examples 1, 2, 4, 5 and 6 pertain to a particularly preferred embodiment of the instant invention.

Preparation of N,1-bis(2,2,6,6-tetramethyl-4-piperidyl)-4-piperidinemethanamine: 223.5 g (1.44 tool) of 2,2,6,6-tetramethyl-4-piperidone, 82.2 g (0.72 tool) of 4-piperidinemethanamine, 0.2 g of benzoic acid and 500 ml of toluene are heated under reflux with azeotropic removal of the water of reaction.

The solvent is removed by heating to 50° C. in vacuo and the residue obtained is dissolved in 800 ml of methanol and hydrogenated at ambient temperature in the presence of 12 g of 5% Pt on carbon under a hydrogen pressure of 40 bar.

After separating off the catalyst by filtration, the solvent is evaporated in vacuo and the residue is crystallised from acetonitrile.

The product obtained melts at 91°–93° C.

Analysis for $C_{24}H_{48}N_4$

Calculated: C=73.41%; H=12.32%; N=14.27%
Found: C=72.80%; H=12.26%; N=14.15%

EXAMPLE 1

Preparation of the Compound of the Formula

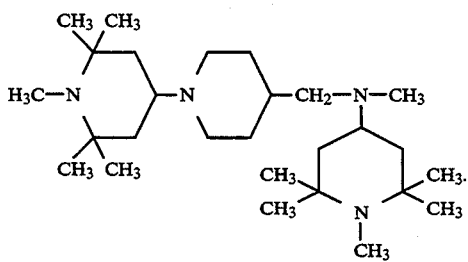

19.6 g (0.05 tool)of N,1-bis(2,2,6,6-tetramethyl-4-piperidyl)-4-piperidinemethanamine are dissolved at ambient temperature in a solution of 20.7 g (0.45 tool) of formic acid in 250 ml of water.

13.5 g (0.45 mol) of paraformaldehyde are added to the solution obtained and the mixture is heated under reflux for 8 hours. After cooling to ambient temperature, a solution of 20 g of sodium hydroxide in 120 ml of water is added; a precipitate forms, which is extracted with dichloromethane.

The organic phase is then separated off, washed with water and dried over $Na_2SO_4$.

Evaporation of the solvent gives a low-melting residue.

Analysis for $C_{27}H_{54}N_4$

Calculated: C=74.59%; H=12.52%; N=12.89%
Found: C=74.57%; H=12.50%; N=12.81%

EXAMPLE 2

Preparation of the Compound of the Formula

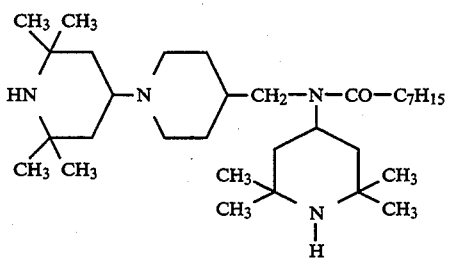

A solution of 9.1 g (0.056 mol) of octanoyl chloride in 20 ml of dichloromethane is added slowly to a solution, cooled to 10° C., of 22 g (0.056 mol) of N,1-bis(2,2,6,6-tetramethyl-4-piperidyl)-4-piperidinemethanamine in 100 ml of dichloromethane.

The solution is then stirred for 2 hours at ambient temperature.

A solution of 2.4 g (0.06 tool) of sodium hydroxide in 50 ml of water is added slowly, while maintaining the temperature at 10° C., and the mixture is stirred for 1 hour at ambient temperature. The organic phase is then separated off, washed with water and dried over $Na_2SO_4$. A low-melting residue is obtained by evaporation of the solvent.

Analysis for $C_{32}H_{62}N_4O$

Calculated: C=74.08%; H=12.04%; N=10.80%
Found: C=73.48%; H=11.98%; N=10.67%

EXAMPLE 3

Preparation of the Compound of the Formula

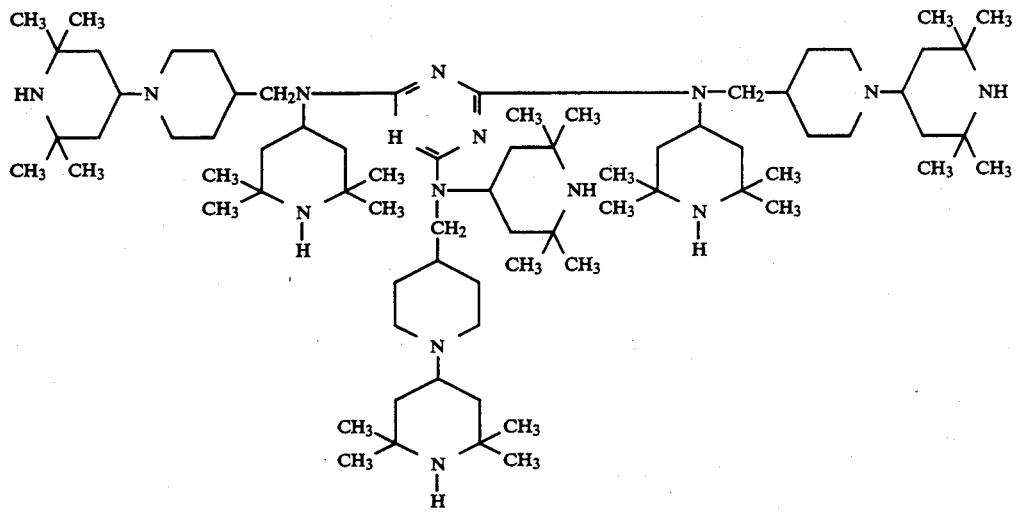

58.9 g (0.15 mol) of N, 1-bis(2,2,6,6-tetramethyl-4-piperidyl)-4-piperidinemethanamine, dissolved in 100 ml of mesitylene, are added slowly to a solution of 9.2 g (0.05 mol) of cyanuric chloride in 100 ml of mesitylene, while maintaining the temperature at 20° C.

After the end of the addition, the mixture is heated for 4 hours at 60° C; 8 g (0.2 mol) of powdered sodium hydroxide are added and the mixture is heated for 10 hours under reflux, with azeotropic removal of the water of reaction.

After cooling to 60° C., the mixture is filtered and evaporated under a reduced pressure.

The residue is then crystallised from a 1:1 acetonitrile/water mixture. The product obtained melts at 165°–166° C.

Analysis for $C_{75}H_{141}N_{15}$

Calculated: C=71.89 %; H=11.34 %; N=16.77%
Found: C=71.30%; H=11.24%; N=16.58%

EXAMPLE 4

Preparation of the Compound of the Formula

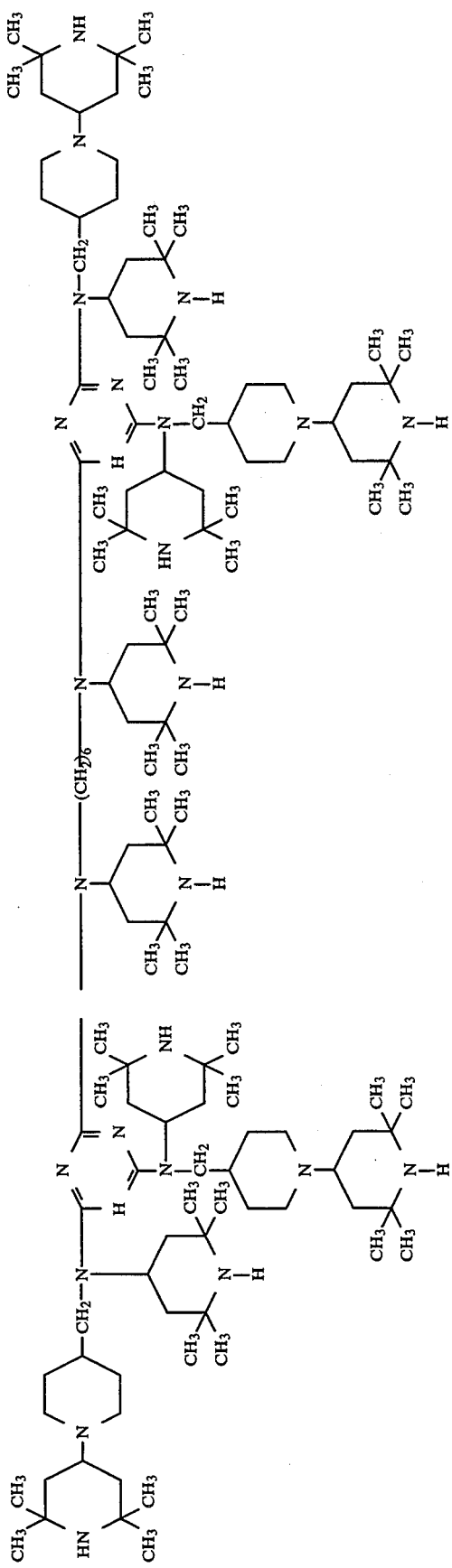

A) Preparation of 2-chloro-4,6-bis[N, 1-bis(2,2,6,6-tetramethyl-4-piperidyl)-4-piperidinemethanamino]-1,3,5-triazine.

A solution of 46.1 g (0.25 tool) of cyanuric chloride in 500 ml of xylene is added slowly to a solution of 196.3 g (0.5 tool) of N,1-bis(2,2,6,6-tetramethyl-4-piperidyl)-4-piperidinemethanamine in 400 ml of xylene, while maintaining the temperature between 20° and 50° C.

The mixture is then stirred for one hour at ambient temperature, 20 g (0.5 mol) of sodium hydroxide dissolved in 100 ml of water are added and the mixture is heated for 2 hours at 100° C.

After cooling to ambient temperature, the aqueous phase is separated off, and the organic layer is dried over Na2SO4, filtered and evaporated under a reduced pressure.

The residue thus obtained is crystallised from a 5:1 ethyl acetate/water mixture. The product obtained melts at 135°–137° C.

Cl=3.96 % (calculated for $C_{51}H_{94}ClN_{11}$=3.95%)

B) 29.6 g (0.033 mol) of 2-chloro-4,6-bis[N, 1-bis(2,2,6,6-tetramethyl-4-piperidyl)-4-piperidinemethanamino]-1,3,5-triazine, 6.3 g (0.016 mol) of N,N'-bis(2,2,6,6-tetramethyl-4-piperidyl)-1,6-hexanediamine and 2.6 g (0.066 mol) of powdered sodium hydroxide in 200 ml of mesitylene are heated under reflux for 10 hours with azeotropic removal of the water of reaction.

After cooling to 70° C., the reaction mixture is filtered and evaporated under a reduced pressure.

The residue is crystallised from acetonitrile.

The product obtained melts at 172°–175° C.

Analysis for $C_{126}H_{236}N_{26}$
Calculated: C=7 1.54%; H=11.24 %; N=17.22%
Found: C=7 1.23%; H=10.76 %; N=17.09%

EXAMPLES 5-6

Following the procedure described in Example 4 and using the corresponding reagents in the appropriate molar ratios, the following compounds of the formula

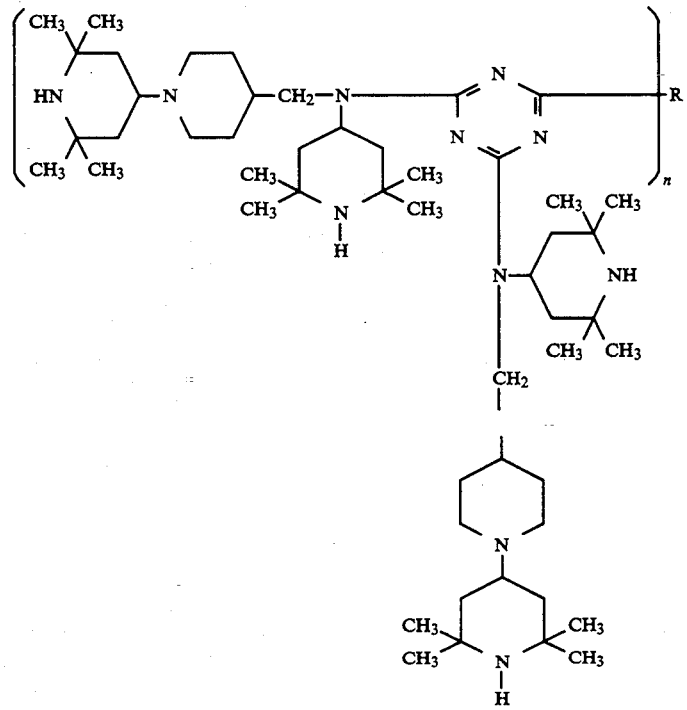

are prepared.

| Example | n | R | m.p. (°C.) |
|---|---|---|---|
| 5 | 3 | —NH—(CH₂)₃—N—(CH₂)₃—NH— | 182–183 |
| 6 | 4 | —NH—(CH₂)₃—N—(CH₂)₂—N—(CH₂)₃—NH— | 186–188 |

EXAMPLE 7

Preparation of the Compound of the Formula

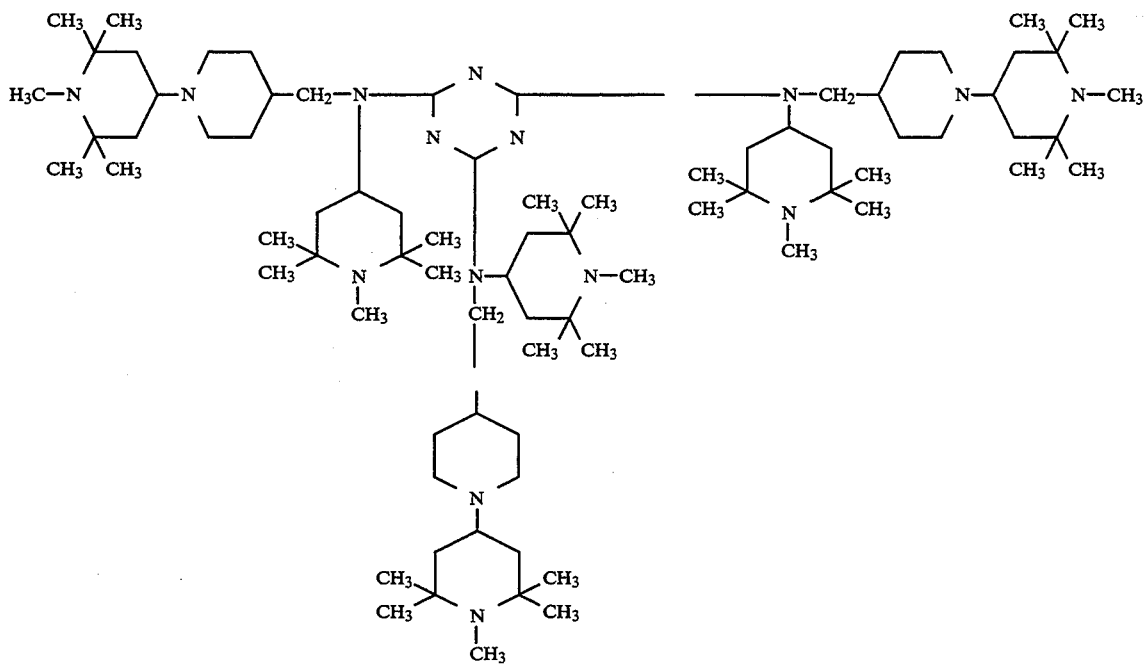

A mixture containing 4.6 g (0.1 mol) of formic acid and 10 g (0.1 mol) of a methanol-free aqueous 30% formaldehyde solution is added in the course of 3 hours to a solution of 18.8 g (0.015 tool) of the compound prepared according to Example 4 in 100 ml of xylene, heated to 110° C., with simultaneous removal of the water added and the water of reaction.

The mixture is then cooled to 70° C., a solution of 6 g of sodium hydroxide in 50 ml of water is added and the mixture is stirred for 30 minutes. After separating off the aqueous phase, the organic layer is washed with water, dried over $Na_2SO_4$ and evaporated under a reduced pressure.

The product obtained melts at 174°–176° C.

Analysis for $C_{81}H_{153}N_{15}$

Calculated: C=72.76%; H=11.53%; N=15.71%
Found: C=72.38%; H=11.51%; N=15.53%

EXAMPLES 8–9

Following the procedure described in Example 7 and using the compounds from Examples 5 and 6, the following compounds of the formula

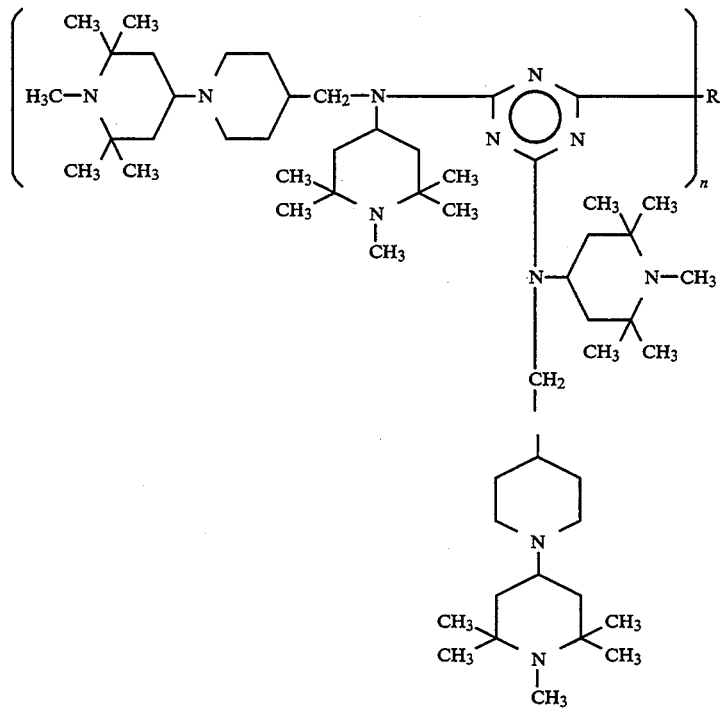

| Example | n | R | m.p. (°C.) |
|---|---|---|---|
| 8 | 2 | —N—(CH₂)₆—N— (bis-2,2,6,6-tetramethyl-1-methylpiperidin-4-yl structure) | 192–195 |
| 9 | 3 | —NH—(CH₂)₃—N—(CH₂)₃—NH— | 185–187 |

EXAMPLE 10

Light-Stabilising Action in Polypropylene Tapes.

1 g of each of the compounds indicated in Table 1, 1.0 g of tris(2,4-di-t-butylphenyl) phosphite, 0.5 g of pentaerythritol tetrakis[3-(3,5-di-t-butyl-4-hydroxyphenyl)-propionate] and 1 g of calcium stearate are mixed in a slow mixer with 1000 g of polypropylene powder of melt index=2 g/10 minutes (measured at 230° C. and 2.16 kg).

The mixtures are extruded at 200°–230° C. to give polymer granules which are then convened into stretched tapes of 50 μm thickness and 2.5 mm width, using a pilot-type apparatus (®Leonard-Sumirago (VA) Italy) operating under the following conditions:
Extruder temperature: 210°–230° C.
Head temperature: 240°–260° C.
Stretch ratio: 1:6

The tapes thus prepared are exposed, mounted on a white card, in a 65 WR Weather-O-Meter (ASTM D2565-85) with a black panel temperature of 63° C.

The residual tenacity is measured on samples taken after various times of exposure to light by means of a constant-speed tensometer; the exposure time in hours ($T_{50}$) needed to halve the initial tenacity is then calculated.

Tapes prepared under the same conditions as indicated above, but without addition of stabilisers according to the present invention, are exposed for comparison.

The results obtained are shown in Table 1.

TABLE 1

| Stabiliser | $T_{50}$ (hours) |
|---|---|
| None | 530 |
| Compound from Example 1 | 3950 |
| Compound from Example 2 | 3500 |
| Compound from Example 4 | 3930 |
| Compound from Example 5 | 3500 |

EXAMPLE 11

Light-Stabilising Action in Polypropylene Fibres.

2.5 g of each of the products indicated in Table 2, 1 g of tris(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°–230° C. to give polymer granules which are then converted into fibres, using a pilot-type apparatus (®Leonard-Sumirago (VA) Italy) operating under the following conditions:
Extruder temperature: 200°–230° C.
Head temperature: 255°–260° C.
Stretch ratio: 1:3.5
Count: 11 dtex per filament.

The fibres thus prepared are exposed, after mounting on a white card, in a model 65 WR Weather-0-Meter (ASTM D2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated. Fibres prepared under the same conditions as indicated above, but without addition of stabilisers according to the invention, are exposed for comparison.

The results obtained are shown in Table 2.

TABLE 2

| Stabiliser | $T_{50}$ (hours) |
|---|---|
| None | 170 |
| Compound from Example 5 | 1700 |
| Compound from Example 8 | 1600 |

What is claimed is:

1. A compound of formula (I)

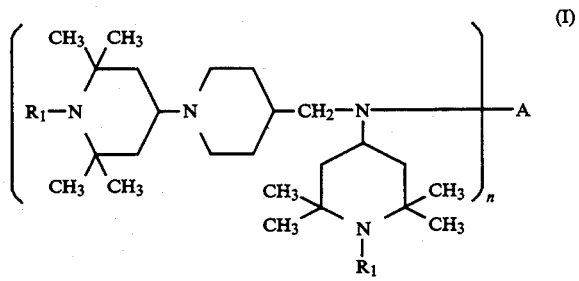

in which $R_1$ is hydrogen, $C_1$–$C_8$alkyl, O, OH, NO, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or mono-, di- or tri-substituted on the phenyl by $C_1$–$C_4$alkyl; or $R_1$ is $C_1$–$C_8$acyl;

n is 1, 2, 3 or 4;

when n is 1, A is $C_1$–$C_{18}$alkyl, $C_3$–$C_6$alkenyl, $C_7$–$C_9$phenylalkyl which is unsubstituted or mono-, di- or tri-substituted on the phenyl by $C_1$–$C_4$alkyl; or A is also one of the groups of the formulae (IIa)–(IIc)

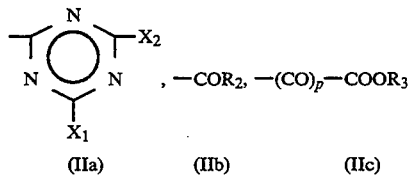

(IIa)   (IIb)   (IIc)

in which $X_1$ and $X_2$ which can be identical or different are a group $-OR_4$, $-SR_4$ or

where $R_4$, $R_5$ and $R_6$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl; $C_3$-$C_{18}$alkenyl, phenyl which is unsubstituted or mono-, di- or tri-substituted by $C_1$-$C_4$alkyl or $C_1$-$C_4$alkoxy; $C_7$-$C_9$phenylalkyl which is unsubstituted or mono-, di- or tri-substituted on the phenyl by $C_1$-$C_4$alkyl; $C_2$-$C_4$alkyl substituted in the 2-, 3- or 4-position by OH, by $C_1$-$C_8$alkoxy, by di($C_1$-$C_4$alkyl)amino or by 1-pyrrolidyl, 1-piperidyl, 4-morpholinyl, 4-methyl-1-piperazinyl or 1-hexahydroazepinyl; tetrahydrofurfuryl or a group of the formula (III)

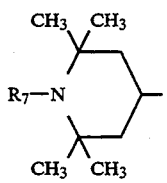

where $R_7$ is as defined for $R_1$; or

is 1-pyrrolidyl, 1-piperidyl, 4-morpholinyl, 4-methyl-1-piperazinyl or 1-hexahydroazepinyl;

$R_2$ is hydrogen, $C_1$-$C_{18}$alkyl, $C_5$-$C_{12}$cycloalkyl which is unsubstituted or mono-, di- or tri-substituted by $C_1$-$C_4$alkyl; $C_2$-$C_{18}$alkenyl, phenyl which is unsubstituted or mono-, di- or tri-substituted by $C_1$-$C_4$alkyl or $C_1$-$C_4$alkoxy and/or monosubstituted by an OH group; $C_7$-$C_9$phenylalkyl which is unsubstituted or mono-, di- or tri-substituted on the phenyl by $C_1$-$C_4$alkyl and/or monosubstituted by an OH group;

p is zero or 1;

$R_3$ is $C_1$-$C_{18}$alkyl, $C_5$-$C_{12}$cycloalkyl which is unsubstituted or mono-, di- or tri-substituted by $C_1$-$C_4$alkyl; $C_3$-$C_{18}$alkenyl, $C_7$-$C_9$phenylalkyl which is unsubstituted or mono-, di- or tri-substituted on the phenyl by $C_1$-$C_4$alkyl; or a group of the formula (III);

when n is 2, A is $C_2$-$C_{12}$alkylene, $C_4$-$C_{12}$alkylene interrupted by 1, 2 or 3 oxygen atoms; 2-hydroxytrimethylene, phenylenedimethylene or one of the groups of the formulae (Va)-(Ve)

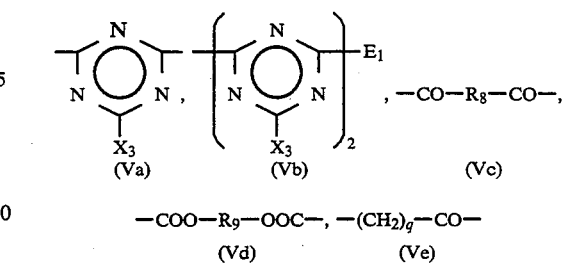

(Va)   (Vb)   (Vc)

$-COO-R_9-OOC-$, $-(CH_2)_q-CO-$
(Vd)                 (Ve)

in which $X_3$ is as defined above for $X_1$ and $X_2$; or $X_3$ is a group of the formula (VI)

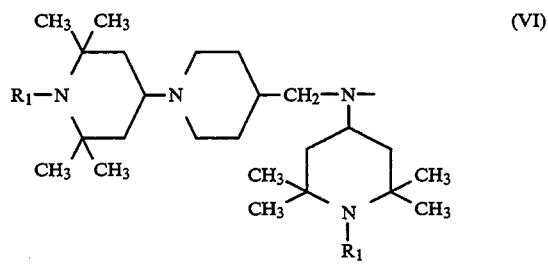

with $R_1$ being as defined above;

$E_1$ is one of the groups of the formulae (VIIa)–(VIIb)

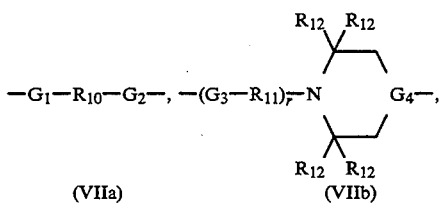

(VIIa)   (VIIb)

in which $G_1$, $G_2$ and $G_3$ which can be identical or different are $-O-$ or

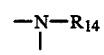

where $R_{14}$ is hydrogen, $C_1$-$C_{18}$alkyl, $C_5$-$C_{12}$cycloalkyl which is unsubstituted or mono-, di- or tri-substituted by $C_1$-$C_4$alkyl; $C_7$-$C_9$phenylalkyl which is unsubstituted or mono-, di- or tri-substituted on the phenyl by $C_1$-$C_4$alkyl; or a group of the formula (III);

$R_{10}$ is $C_2$-$C_{12}$alkylene, $C_4$-$C_{12}$alkylene interrupted by 1, 2 or 3 oxygen atoms or by 1 or 2

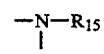

groups where $R_5$ is as defined above for $R_{14}$ or is $C_1$-$C_8$acyl or ($C_1$-$C_8$alkoxy)carbonyl; $C_5$-$C_7$cycloalkylene, $C_5$-$C_7$cycloalkylenedi($C_1$-$C_4$alkylene), $C_1$-$C_4$alkylenedi($C_5$-$C_7$cycloalkylene), $C_2$-$C_4$alkylidenedi($C_5$-$C_7$cycloalkylene), phenylene, phenylenedi($C_1$-$C_4$alkylene), $C_1$-$C_4$alkylenediphenylene or $C_2$-$C_4$alkylidenediphenylene;

$R_{11}$ is $C_2$-$C_6$alkylene;

$G_4$ is one of the groups $>N-(R_{11}-G_3)_s-$, $>CH-O-$ or

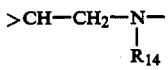

with R$_{14}$ being as defined above;

r and s which can be identical or different are zero or 1;

R$_{12}$ is hydrogen or, when r is 1 and G$_4$ is >CH—O—, R$_{12}$ is also methyl;

R$_8$ is a direct bond, C$_1$-C$_{12}$alkylene, C$_2$-C$_4$alkenylene, cyclohexylene, cyclohexenylene or phenylene;

R$_9$ is C$_2$-C$_{12}$alkylene, C$_4$-C$_{12}$alkylene interrupted by 1, 2 or 3 oxygen atoms; C$_5$-C$_7$cycloalkylene, C$_5$-C$_7$cycloalkylenedi(C$_1$-C$_4$alkylene) or C$_2$-C$_4$alkylidenedi(C$_5$-C$_7$cycloalkylene);

q is zero or an integer from 1 to 10;

when n is 3, A is aliphatic C$_4$-C$_{18}$triacyl, aromatic C$_9$-C$_{18}$triacyl or a group of the formula (VIII)

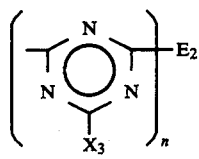

(VIII)

in which X$_3$ is as defined above;

E$_2$ is one of the groups of the formulae (IXa)–(IXc)

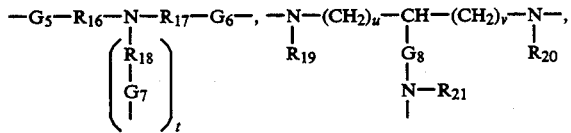

(IXa)     (IXb)

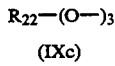

(IXc)

in which G$_5$, G$_6$ and G$_7$ which can be identical or different are as defined above for G$_1$, G$_2$ and G$_3$;

R$_{16}$, R$_{17}$ and R$_{18}$ which can be identical or different are C$_2$-C$_6$alkylene;

t is zero or 1;

R$_{19}$, R$_{20}$ and R$_{21}$ which can be identical or different are as defined above for R$_{14}$;

G$_8$ is a direct bond or —CH$_2$—;

u and v which can be identical or different are integers from 2 to 6;

R$_{22}$ is C$_3$-C$_{12}$alkanetriyl;

when n is 4, A is aliphatic C$_6$-C$_{18}$tetraacyl, aromatic C$_{10}$-C$_{18}$tetraacyl or a group of the formula (Xa)

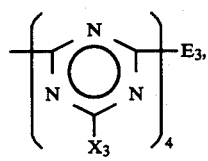

(Xa)

in which X$_3$ is as defined above;

E$_3$ is a group of the formulae (XIa)–(XIc)

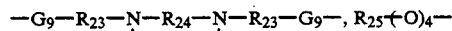

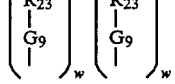

(XIa)

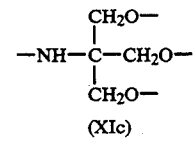

(XIc)

in which G$_9$ is as defined above for G$_1$, G$_2$ and G$_3$;

R$_{23}$ and R$_{24}$ which can be identical or different are C$_2$-C$_6$alkylene;

w is zero or 1; and

R$_{25}$ is C$_4$-C$_{12}$alkanetetrayl.

2. A compound of formula (I) according to claim 1, in which R$_1$ and R$_7$ which can be identical or different are hydrogen, C$_1$-C$_4$alkyl, OH, C$_6$-C$_{12}$alkoxy, C$_5$-C$_8$cycloalkoxy, allyl, benzyl or acetyl.

3. A compound of formula (I) according to claim 1, in which n is 1, 2, 3 or 4;

when n is 1, A is C$_1$-C$_{18}$alkyl, C$_3$-C$_4$alkenyl, benzyl which is unsubstituted or mono-, di- or tri-substituted on the phenyl by C$_1$-C$_4$alkyl; or A is one of the groups of the formulae (IIa)–(IIc) in which X$_1$ and X$_2$ which can be identical or different are a group —OR$_4$, —SR$_4$ or

where R$_4$, R$_5$ and R$_6$ which can be identical or different are hydrogen, C$_1$-C$_{18}$alkyl, C$_5$-C$_8$cycloalkyl which is unsubstituted or mono-, di- or tri-substituted by C$_1$-C$_4$alkyl; C$_3$-C$_{18}$alkenyl, phenyl which is unsubstituted or mono-, di- or tri-substituted by C$_1$-C$_4$alkyl or C$_1$-C$_4$alkoxy; benzyl which is unsubstituted or mono-, di- or tri-substituted on the phenyl by C$_1$-C$_4$alkyl; C$_2$-C$_3$alkyl substituted in the 2- or 3-position by OH, by C$_1$-C$_4$alkoxy, by di(C$_2$-C$_4$alkyl)amino or by a group

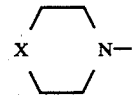

where X is a direct bond, —O—, —CH$_2$— or —CH$_2$CH$_2$—; tetrahydrofurfuryl or a group of the formula (III), or the group

is a group

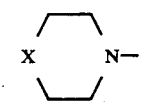

as defined above;

R$_2$ is hydrogen, C$_1$–C$_{17}$alkyl, C$_5$–C$_8$cycloalkyl which is unsubstituted or mono-, di- or tri-substituted by C$_1$–C$_4$alkyl; C$_2$–C$_{17}$alkenyl, phenyl which is unsubstituted or mono-, di- or tri-substituted by C$_1$–C$_4$alkyl or C$_1$–C$_4$alkoxy and/or monosubstituted by an OH group; benzyl or phenylethyl which, both, are unsubstituted or mono-, di- or tri-substituted on the phenyl by C$_1$–C$_4$alkyl and/or monosubstituted by an OH group;

p is zero or 1;

R$_3$ is C$_1$–C$_{18}$alkyl, C$_5$–C$_{18}$cycloalkyl which is unsubstituted or mono-, di- or tri-substituted by C$_1$–C$_4$alkyl; C$_3$–C$_{18}$alkenyl, benzyl which is unsubstituted or mono-, di- or tri-substituted on the phenyl by C$_1$–C$_4$alkyl; or a group of the formula (III);

when n is 2, A is C$_2$–C$_{10}$alkylene, C$_4$–C$_{10}$alkylene interrupted by 1, 2 or 3 oxygen atoms; 2-hydroxytrimethylene, phenylenedimethylene or one of the groups of the formulae (Va)–(Ve) in which X$_3$ is as defined above for X$_1$ and X$_2$ or is a group of the formula (VI);

E$_1$ is one of the groups of the formulae (VIIa)–(VIIb) in which G$_1$, G$_2$ and G$_3$ which can be identical or different are —O— or

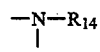

where R$_{14}$ is hydrogen, C$_1$–C$_{18}$alkyl, C$_5$–C$_8$cycloalkyl which is unsubstituted or mono-, di- or tri-substituted by C$_1$–C$_4$alkyl; benzyl which is unsubstituted or mono-, di- or tri-substituted on the phenyl by C$_1$–C$_4$alkyl; or a group of the formula (III);

R$_{10}$ is C$_2$–C$_{10}$alkylene, C$_4$–C$_{10}$alkylene interrupted by 1, 2 or 3 oxygen atoms or by 1 or 2

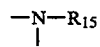

groups where R$_{15}$ is as defined above for R$_{14}$ or is C$_1$–C$_6$acyl or(C$_1$–C$_6$alkoxy)carbonyl; cyclohexylene, cyclohexylenedimethylene, methylenedicyclohexylene, isopropylidenedicyclohexylene, phenylene, phenylenedimethylene, methylenediphenylene, or isopropylidenediphenylene;

R$_{11}$ is C$_2$–C$_4$alkylene;

G$_4$ is >N—(R$_{11}$–G$_3$)$_s$—, >CH—O— or

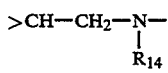

with R$_{14}$ being as defined above;

r and s which can be identical or different are zero or 1;

R$_{12}$ is hydrogen or, when r is 1 and G$_4$ is >CH—O—, R$_{12}$ is also methyl;

R$_8$ is a direct bond, C$_1$–C$_{10}$alkylene, vinylene, cyclohexylene or phenylene;

R$_9$ is C$_2$–C$_{10}$alkylene, C$_4$–C$_{10}$alkylene interrupted by 1, 2 or 3 oxygen atoms; cyclohexylene, cyclohexylenedimethylene or isopropylidenedicyclohexylene;

q is zero or an integer from 1 to 5;

when n is 3, A is aliphatic C$_4$–C$_{12}$triacyl, aromatic C$_9$–C$_{12}$triacyl or a group of the formula (VIII) in which X$_3$ is as defined above and E$_2$ is one of the groups of the formulae (IXa)—(IXc) in which G$_5$, G$_6$ and G$_7$ which can be identical or different are as defined above for G$_1$, G$_2$ and G$_3$;

R$_{16}$, R$_{17}$ and R$_{18}$ which can be identical or different are C$_2$–C$_6$alkylene;

t is zero or 1;

R$_{19}$, R$_{20}$ and R$_{21}$ which can be identical or different are as defined above for R$_{14}$;

G$_8$ is a direct bond or —CH$_2$—;

u and v which can be identical or different are integers from 2 to 6; and

R$_{22}$ is C$_3$–C$_{10}$alkanetriyl;

when n is 4, A is aliphatic C$_6$–C$_{12}$tetraacyl, aromatic C$_{10}$–C$_{12}$tetraacyl or a group of the formula (Xa) in which X$_3$ is as defined above and E$_3$ is a group of the formula (XIa)–(XIc) in which G$_9$ is as defined above for G$_1$, G$_2$ and G$_3$;

R$_{23}$ and R$_{24}$ which can be identical or different are C$_2$–C$_6$alkylene;

w is zero or 1; and

R$_{25}$ is C$_4$–C$_8$alkanetetrayl.

4. A compound of formula (I) according to claim 1, in which n is 1, 2, 3 or 4;

when n is 1, A is methyl, C$_4$–Q$_{18}$alkyl, allyl, benzyl or one of the groups of the formulae (IIa)–(IIc) in which X$_1$ and X$_2$ which can be identical or different are a group —OR$_4$, —SR$_4$ or

where R$_4$, R$_5$ and R$_6$ which can be identical or different are hydrogen, C$_1$–C$_{12}$alkyl, cyclohexyl which is unsubstituted or mono-, di- or tri-substituted by C$_1$–C$_4$alkyl; allyl, undecenyl, phenyl, benzyl, C$_2$–C$_3$alkyl substituted in the 2- or 3-position by OH, by C$_1$–C$_4$alkoxy, by dimethylamino, by diethylamino or by 4-morpholinyl; tetrahydrofurfuryl or a group of the formula (III), or the group

is 4-morpholinyl;

R$_2$ is C$_2$–C$_7$alkyl, cyclohexyl which is unsubstituted or mono-, di- or tri-substituted by C$_1$–C$_4$alkyl; C$_2$–C$_{10}$alkenyl, phenyl, t-butylphenyl, 3,5-di-t-butyl-4-hydroxyphenyl, benzyl or 2-(3,5-di-t-butyl-4-hydroxyphenyl)-ethyl;

p is zero or 1;

R$_3$ is C$_2$–C$_{18}$alkyl, cyclohexyl which is unsubstituted or mono-, di- or tri-substituted by C$_1$–C$_4$alkyl; allyl, undecenyl, oleyl, benzyl or a group of the formula (III);

when n is 2, A is C$_2$–C$_8$alkylene, C$_4$–C$_8$alkylene interrupted by 1 or 2 oxygen atoms; 2-hydroxytrimethylene, phenylenedimethylene or one of the groups of the formulae (Va)–(Ve) in which X$_3$ is as defined above for X$_1$ and X$_2$ or is a group of the formula (VI);

E$_1$ is one of the groups of the formulae (VIIa)–(VIIb) in which G$_1$, G$_2$ and G$_3$ which can be identical or different are —O— or $$-\overset{\displaystyle |}{\underset{\displaystyle |}{N}}-R_{14}$$

where $R_{14}$ is hydrogen, $C_1$-$C_{12}$alkyl, cyclohexyl which is unsubstituted or mono-, di- or tri-substituted by $C_1$-$C_4$alkyl; benzyl or a group of the formula (III);

$R_{10}$ is $C_2$-$C_8$alkylene, $C_4$-$C_{10}$alkylene interrupted by 1, 2 or 3 oxygen atoms or by 1 or 2

$$-\overset{\displaystyle |}{N}-R_{15}$$

groups where $R_{15}$ is as defined above for $R_{14}$ or is $C_1$-$C_4$acyl or ($C_1$-$C_4$alkoxy)carbonyl; cyclohexylenedimethylene, methylenedicyclohexylene, isopropylidenedicyclohexylene, phenylenedimethylene or isopropylidenediphenylene;

$R_{11}$ is $C_2$-$C_3$alkylene;

$G_4$ is $>N$—$(R_{11}$-$G_3)_s$— or $>CH$—O—, r and s which can be identical or different are zero or 1;

$R_{12}$ is hydrogen or, when r is 1 and $G_4$ is $>CH$—O—, $R_{12}$ is also methyl;

$R_8$ is a direct bond or $C_1$-$C_8$alkylene;

$R_9$ is $C_2$-$C_8$alkylene, $C_4$-$C_8$alkylene interrupted by 1 or 2 oxygen atoms; cyclohexylenedimethylene or isopropylidenedicyclohexylene; and q is zero or an integer from 1 to 3;

when n is 3, A is aliphatic $C_4$-$C_8$triacyl, benzenetricarbonyl or a group of the formula (VIII) in which $X_3$ is as defined above and $E_2$ is one of the groups of the formulae (IXa)–(IXc) in which $G_5$, $G_6$ and $G_7$ which can be identical or different are as defined above for $G_1$, $G_2$ and $G_3$;

$R_{16}$, $R_{17}$ and $R_{18}$ which can be identical or different are $C_2$-$C_4$alkylene;

t is zero or 1;

$R_{19}$, $R_{20}$ and $R_{21}$ which can be identical or different are as defined above for $R_{14}$;

$G_8$ is a direct bond or —$CH_2$—;

u and v which can be identical or different are integers from 3 to 6; and $R_{22}$ is $C_3$-$C_6$alkanetriyl;

when n is 4, A is aliphatic $C_6$-$C_8$tetraacyl, benzenetetracarbonyl or a group of the formula (Xa) in which $X_3$ is as defined above and $E_3$ is a group of the formulae (XIa)–(XIc) in which $G_9$ is as defined above for $G_1$, $G_2$ and $G_3$;

$R_{23}$ and $R_{24}$ which can be identical or different are $C_2$-$C_4$alkylene;

w is zero or 1; and $R_{25}$ is $C_4$-$C_6$alkanetetrayl.

5. A compound of formula (I) according to claim 1, in which n is 1, 2, 3 or 4;

when n is 1, A is methyl, $C_8$-$C_{18}$alkyl or one of the groups of the formulae (IIa)–(IIc) in which $X_1$ and $X_2$ which can be identical or different are a group —$OR_4$ or $$-\overset{\displaystyle |}{\underset{\displaystyle R_5}{N}}-R_6$$

where $R_4$ is $C_1$-$C_8$alkyl or a group of the formula (III), $R_5$ and $R_6$ which can be identical or different are $C_1$-$C_8$alkyl, cyclohexyl, $C_2$-$C_3$alkyl substituted in the 2- or 3-position by methoxy, by ethoxy, by dimethylamino, by diethylamino or by 4-morpholinyl; tetrahydrofurfuryl or a group of the formula (III) or the group $$-\overset{\displaystyle |}{\underset{\displaystyle R_5}{N}}-R_6$$

is 4-morpholinyl; or $R_5$ is also hydrogen;

$R_2$ is $C_3$-$C_{17}$alkyl, cyclohexyl, phenyl, 3,5-di-t-butyl-4-hydroxyphenyl or 2-(3,5-di-t-butyl-4-hydroxyphenyl)-ethyl;

p is zero;

$R_3$ is $C_4$-$C_{18}$alkyl, cyclohexyl, t-butylcyclohexyl or a group of the formula (III);

when n is 2, A is one of the groups of the formulae (Va)—(Ve) in which $X_3$ is as defined above for $X_1$ and $X_2$ or is a group of the formula (VI) $E_1$ is one of the groups of the formulae (VIIa)–(VIIb) in which $G_1$ and $G_2$ which can be identical or different are —O— or $$\overset{\diagdown}{\underset{\diagup}{N}}-R_{14}$$

where $R_{14}$ is hydrogen, $C_1$-$C_8$alkyl, cyclohexyl or a group of the formula (III);

$R_{10}$ is $C_2$-$C_6$alkylene, $C_6$-$C_{10}$alkylene interrupted by 2 or 3 oxygen atoms; cyclohexylenedimethylene or methylenedicyclohexylene, the group (VIIb) is one of the groups $$-\left[\overset{\displaystyle |}{\underset{\displaystyle R_{14}}{N}}-(CH_2)_{2\text{-}3}\right]_r-N\diagup\diagdown N-\left[(CH_2)_{2\text{-}3}-\overset{\displaystyle |}{\underset{\displaystyle R_{14}}{N}}\right]_s-$$

and $$-O-(CH_2)_2-N\underset{CH_3\;\;\;CH_3}{\overset{CH_3\;\;\;CH_3}{\diagdown\diagup}}-O-$$

where r and s which can be identical or different are zero or 1;

$R_{14}$ is as defined above;

$R_8$ is $C_2$-$C_8$alkylene;

$R_9$ is $C_4$-$C_8$alkylene or isopropylidenedicyclohexylene; and q is zero or 1;

when n is 3, A is a group of the formula (VIII) in which $X_3$ is as defined above and $E_2$ is a group of the formula (IXa) or (IXb) in which $G_5$ and $G_6$ which can be identical or different are as defined above for $G_1$ and $G_2$;

$R_{16}$ and $R_{17}$ which can be identical or different are $C_2$-$C_3$alkylene;

t is zero;

$R_{19}$, $R_{20}$ and $R_{21}$ are as defined above for $R_{14}$;

$G_8$ is a direct bond or —$CH_2$—;

u and v which can be identical or different are integers from 3 to 5;

when n is 4, A is a group of the formula (Xa) in which $X_3$ is as defined above and $E_3$ is a group of the formula (XIa) in which
$G_9$ is as defined above for $G_1$ and $G_2$;
$R_{23}$ and $R_{24}$ which can be identical or different are $C_2$-$C_3$alkylene; and
w is zero or 1.

6. A compound of formula (I) according to claim 1, in which $R_1$ is hydrogen or methyl;
n is 1, 2, 3 or 4;
when n is 1, A is methyl or one of the groups of the formulae (IIa)–(IIc) in which $X_1$ and $X_2$ which can be identical or different are a group —$OR_4$ or

where $R_4$ is $C_1$-$C_4$alkyl, 2,2,6,6-tetramethyl-4-piperidyl or 1,2,2,6,6-pentamethyl-4-piperidyl, $R_5$ and $R_6$ which can be identical or different are $C_1$-$C_4$alkyl, cyclohexyl, tetrahydrofurfuryl, 2,2,6,6-tetramethyl-4-piperidyl or 1,2,2,6,6-pentamethyl-4-piperidyl or the group

is 4-morpholinyl; or $R_5$ is also hydrogen;
$R_2$ is $C_5$-$C_{17}$alkyl;
p is zero;
$R_3$ is $C_6$-$C_{18}$alkyl,
when n is 2, A is one of the groups of the formulae (Va)–(Vd) in which $X_3$ is as defined above for $X_1$ and $X_2$ or is a group of the formula (VI);
$E_1$ is a group

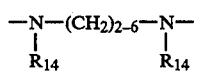

where $R_{14}$ is hydrogen, methyl, 2,2,6,6-tetramethyl-4-piperidyl or 1,2,2,6,6-pentamethyl-4-piperidyl;
$R_8$ is $C_4$-$C_8$alkylene; and
$R_9$ is $C_4$-$C_6$alkylene, and, when n is 3, A is a group of the formula (VIII) in which $X_3$ is as defined above and $E_2$ is a group

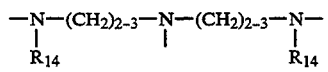

where $R_{14}$ is as defined above, and,
when n is 4, A is a group of the formula (Xa) in which $X_3$ is as defined above and $E_3$ is a group

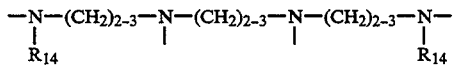

with $R_{14}$ being as defined above.

7. A compound of formula (I) according to claim 1, in which $R_1$ is hydrogen or methyl;
n is 1, 2, 3 or 4;
when n is 1, A is methyl or a group of the formula (IIb) in which $R_2$ is $C_5$-$C_7$alkyl;
when n is 2, A is a group of the formula (Va) or (Vb), in which $X_3$ is a group of the formula (VI) and $E_1$ is a group

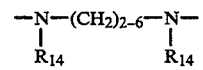

where $R_{14}$ is 2,2,6,6-tetramethyl-4-piperidyl or 1,2,2,6,6-pentamethyl-4-piperidyl;
when n is 3, A is a group of the formula (VIH) in which $X_3$ is as defined above and $E_2$ is a group

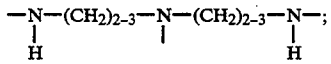

and,
when n is 4, A is a group of the formula (Xa) in which $X_3$ is as defined above and $E_3$ is a group

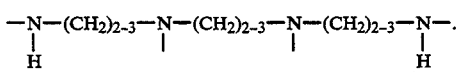

* * * * *